US008961959B2

(12) United States Patent
Larsen et al.

(10) Patent No.: US 8,961,959 B2
(45) Date of Patent: Feb. 24, 2015

(54) GLUCOSYLCERAMIDE SYNTHASE INHIBITORS AND THERAPEUTIC METHODS USING THE SAME

(71) Applicant: The Regents of the University of Michigan, Ann Arbor, MI (US)

(72) Inventors: Scott Larsen, South Lyon, MI (US); Akira Abe, Ann Arbor, MI (US); Liming Shu, Ann Arbor, MI (US); Michael William Wilson, Ann Arbor, MI (US); Richard F. Keep, Ann Arbor, MI (US); James A. Shayman, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 101 days.

(21) Appl. No.: 13/652,016

(22) Filed: Oct. 15, 2012

(65) Prior Publication Data

US 2013/0095089 A1    Apr. 18, 2013

Related U.S. Application Data

(60) Provisional application No. 61/548,134, filed on Oct. 17, 2011.

(51) Int. Cl.
| | | |
|---|---|---|
| *A61K 38/43* | (2006.01) | |
| *A01N 43/36* | (2006.01) | |
| *A61K 31/40* | (2006.01) | |
| *A61K 48/00* | (2006.01) | |
| *A01N 33/18* | (2006.01) | |
| *A01N 33/24* | (2006.01) | |
| *A61K 31/045* | (2006.01) | |
| *C07D 405/00* | (2006.01) | |
| *C07D 207/08* | (2006.01) | |
| *C07D 207/46* | (2006.01) | |
| *C07D 295/04* | (2006.01) | |
| *A61K 45/06* | (2006.01) | |
| *C07D 319/18* | (2006.01) | |
| *C07D 295/125* | (2006.01) | |
| *C07D 295/135* | (2006.01) | |

(52) U.S. Cl.
CPC .............. *A61K 45/06* (2013.01); *C07D 319/18* (2013.01); *C07D 295/125* (2013.01); *C07D 295/135* (2013.01); *A61K 31/40* (2013.01)

USPC .......... 424/94.1; 514/422; 514/44 R; 514/728; 548/526; 548/568; 548/569

(58) Field of Classification Search
None
See application file for complete search history.

(56) References Cited

U.S. PATENT DOCUMENTS

| | | |
|---|---|---|
| 5,302,609 A | 4/1994 | Shayman et al. |
| 5,472,969 A | 12/1995 | Platt et al. |
| 5,525,616 A | 6/1996 | Platt et al. |
| 5,916,911 A | 6/1999 | Shayman et al. |
| 5,945,442 A | 8/1999 | Shayman et al. |
| 5,952,370 A | 9/1999 | Shayman et al. |
| 6,030,995 A | 2/2000 | Shayman et al. |
| 6,051,598 A | 4/2000 | Shayman et al. |
| 6,255,336 B1 | 7/2001 | Shayman et al. |
| 6,569,889 B2 | 5/2003 | Shayman et al. |
| 6,610,703 B1 | 8/2003 | Jacob et al. |
| 6,855,830 B2 | 2/2005 | Hirth et al. |
| 6,916,802 B2 | 7/2005 | Shayman et al. |
| 7,196,205 B2 | 3/2007 | Siegel et al. |
| 7,253,185 B2 | 8/2007 | Shayman et al. |
| 7,615,573 B2 | 11/2009 | Siegel et al. |
| 2010/0256216 A1* | 10/2010 | Siegel et al. .................. 514/422 |

FOREIGN PATENT DOCUMENTS

| | | |
|---|---|---|
| WO | WO-2008/150486 A2 | 12/2008 |
| WO | WO-2009/045503 A1 | 4/2009 |
| WO | WO 2009/117150 * | 9/2009 |
| WO | WO-2009/117150 A2 | 9/2009 |
| WO | WO 2010/014554 * | 2/2010 |
| WO | WO-2010/014554 A1 | 2/2010 |
| WO | WO-2010/039256 A1 | 4/2010 |

OTHER PUBLICATIONS

Dulsat et al. (Drugs Fut 2009, 34(1): 23, abstract, 2009).*
International Search Report in PCT/US2012/060244, dated Mar. 26, 2013.

* cited by examiner

*Primary Examiner* — Jeffrey S Lundgren
*Assistant Examiner* — William Lee
(74) *Attorney, Agent, or Firm* — Marshall, Gerstein & Borun LLP

(57) ABSTRACT

Glucosylceramide synthase inhibitors and compositions containing the same are disclosed. Methods of using the glucosylceramide synthase inhibitors in the treatment of diseases and conditions wherein inhibition of glucosylceramide synthase provides a benefit, like Gaucher disease and Fabry disease, also are disclosed.

7 Claims, 6 Drawing Sheets

GLUCOSYLCERAMIDE SYNTHASE INHIBITORS AND THERAPEUTIC METHODS USING THE SAME

CROSS REFERENCE TO RELATED APPLICATIONS

This application claims the benefit of U.S. provisional Patent Application No. 61/548,134, filed Oct. 17, 2011, incorporated herein by reference in its entirety.

GOVERNMENT FUNDING

This invention was made with government support under Grant No. NIH R21NS065492 01A1 awarded by National Institutes of Health. The government has certain rights in the invention.

FIELD OF THE INVENTION

The present invention relates to glucosylceramide synthase (GCS) inhibitors and to therapeutic methods of treating conditions and diseases wherein inhibition of GCS provides a benefit.

BACKGROUND OF THE INVENTION

Lysosomal storage diseases (LSDs), such as Gaucher disease and Fabry disease, occur when glycolipids accumulate in lysosomes due to defect in their catabolism. Two general strategies exist for the treatment of lysosomal storage diseases. The first strategy includes the replacement or restoration of the defective or absent catabolizing enzyme (e.g., the infusion of recombinant enzyme, chaperone therapy, bone marrow transplantation, or gene therapy) (1). Enzyme replacement therapy is clinically approved for lysosomal storage diseases with peripheral manifestations, but is limited by the inability of the infused recombinant enzyme to distribute into the CNS, and by the frequent development of auto-antibodies to the protein in patients carrying null mutations.

The second strategy involves synthesis inhibition therapy (2). Synthesis inhibition is a more recent therapeutic approach, and has focused on identifying small molecule inhibitors of GCS. Two classes of these inhibitors have been described, including imino sugars and analogues of D-threo-1-phenyl-2-decanoylamino-3-morpholino-propanol (PDMP) (3). The imino sugar N-butyldeoxynojirimycin (NBDNJ) is limited by its micromolar level inhibitory activity and limited specificity against the synthase. The limited specificity is associated with a high level of undesired effects resulting from secondary sites of action unrelated to glycolipid synthesis inhibition. These effects most notably include diarrhea, weight loss, and tremor, which limits the approved use of NBDNJ in the United States (4). One advantage of NBDNJ over the PDMP based homologs reported to date is its ability to distribute into the CNS. However, a recent study raised questions with respect to the ability of NBDNJ to lower CNS glycolipid levels (K. M. Ashe et al., *Plos One* 6:e21758 (2011)).

A number of GCS inhibitors have been disclosed, for example, in U.S. Pat. Nos. 5,302,609; 5,472,969; 5,525,616; 5,916,911; 5,945,442; 5,952,370; 6,030,995; 6,051,598; 6,255,336; 6,569,889; 6,610,703; 6,660,794; 6,855,830; 6,916,802; 7,253,185; 7,196,205; and 7,615,573. Additional GCS inhibitors and treatments are disclosed in WO 2008/150486; WO 2009/117150; and WO 2010/014554.

A compound that is currently in clinical trials and structurally related to PDMP is N-((1R,2R)-1-(2,3-dihydrobenzo[b][1,4]dioxin-6-yl)-1-hydroxy-3-(pyrrolidin-1-yl)propan-2-yl)octanamide, also known as Genz-112638 and eliglustat tartrate (5). Recent phase 2 clinical trials using this drug for type 1 Gaucher disease demonstrated an efficacy equal to or greater than that for recombinant β-glucocerebrosidase, as evidenced by reversal of spleen and liver enlargement, correction of anemia, and improvements in thrombocytopenia and bone density (6). Phase 3 trials with eliglustat tartrate are currently in progress. Experimental data also support a potential role for eliglustat tartrate in the treatment of Fabry disease, another lysosomal storage disease with peripheral manifestations (7).

GSC inhibition also is expected to treat six other lysosomal storage diseases with CNS involvement, including early and late onset Tay-Sachs disease, Sandhoff disease, GM1 gangliosidosis, and types 2 and 3 Gaucher disease. For example, an experimental model of genetic epistasis demonstrated markedly improved survival in a mouse model of Sandhoff disease that also lack GM2 synthase (8). However, drug distribution studies indicate that eliglustat tartrate is not transported across the blood brain barrier (BBB) (5). A possible basis for the poor brain distribution of eliglustat tartrate may be that the drug is a substrate for the p-glycoprotein (MDR1) transporter, resulting in efflux of the drug.

Compounds that inhibit GCS have the potential to treat conditions associated with glycolipid accumulation. However, present day GCS inhibitors are limited by poor CNS penetration and/or low activity. An important advance in the art would be the discovery of GCS inhibitors, and particularly GCS inhibitors capable of crossing the BBB, that are useful in the treatment of diseases wherein GCS inhibition provides a benefit, such as type I, II, or III Gaucher disease, Fabry disease, Tay-Sachs disease, Sandhoff disease, diabetes, lupus, and other diseases and conditions associated with glycolipid accumulation in lysosomes. Accordingly, a need still exists in the art for efficacious compounds, compositions, and methods useful in the treatment of such diseases, alone or in conjunction with other therapies used to treat these diseases and conditions. The present invention is directed to meeting this need.

SUMMARY OF THE INVENTION

The present invention is directed to inhibitors of GCS, to compositions comprising the inhibitors, and to methods of using the inhibitors in a therapeutic treatment of conditions and diseases wherein inhibition of GCS provides a benefit. The present compounds are potent inhibitors of GCS, and in some embodiments are capable of crossing the BBB.

More particularly, the present invention is directed to compounds having a structural formula (I):

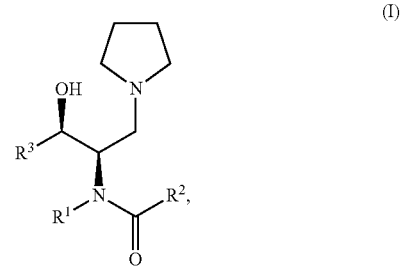

wherein $R^1$ is H or $C_{1-3}$alkyl;
$R^2$ is (i) —$(CH_2)_{1-3}C_6H_5$, with the proviso that $R^1$ is —$C_{1-3}$alkyl,
(ii) —$CH_2$—$C(R^a{}_2)_{1,2}$—$C_6H_5$ wherein $R^a$ independently is H or $C_{1-3}$alkyl, with the proviso that at least one $R^a$ is $C_{1-3}$alkyl, —$(CH_2)_{1,2}NHC_6H_5$,     (iii)

—CH═CHC$_6$H$_5$,     (iv)

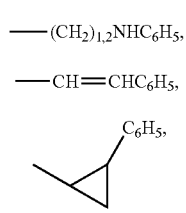 (v)

wherein for (i) through (v) the $C_6H_5$ group optionally is substituted with one or two of -halo or —$OR^a$, or

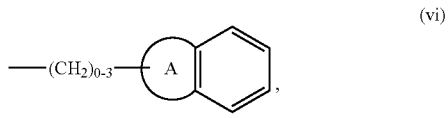 (vi)

wherein the fused ring A is a 4- to 8-membered ring, saturated or partially unsaturated, and comprising carbon atoms and optionally one or two heteroatoms selected from O, S, and $NR^a$, and wherein the fused phenyl ring is optionally substituted with one or two substituents; and
$R^3$ is

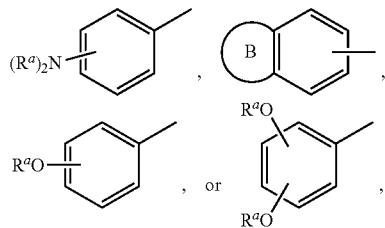

wherein the fused ring B is a five- or six-membered ring, saturated or partially or fully unsaturated, comprising carbon atoms and one or two heteroatoms selected from O, S, and $NR^a$, and wherein the phenyl ring is optionally substituted with one or two substitutents;
or a pharmaceutically acceptable salt, hydrate, solvate, or prodrug thereof.

In one embodiment, the present invention provides a method of treating a condition or disease of interest by administering a therapeutically effective amount of a compound of structural formula (I) to an individual in need thereof. The disease or condition, for example, Gaucher disease, Fabry disease, Sandhoff disease, and Parkinson's disease, is treatable by inhibition of GCS.

In yet another embodiment, the present invention provides a method of treating a subject having type 2 diabetes comprising administering to the subject a therapeutically effective amount of a compound of structural formula (I).

A method of treating a subject having renal hypertrophy or hyperplasia associated with diabetic nephropathy also is included in the invention. The method comprises administering to the subject a therapeutically effective amount of a compound of structural formula (I).

A method of decreasing plasma TNF-α in a subject in need thereof also is included in the present invention. The method comprises administering to the subject a therapeutically effective amount of a compound of structural formula (I).

A method of lowering blood glucose levels in a subject in need thereof also is included in the present invention. The method comprises administering to the subject a therapeutically effective amount of a compound of structural formula (I).

A method of decreasing glycated hemoglobin levels in a subject in need thereof also is included in the present invention. The method comprises administering to the subject a therapeutically effective amount of a compound of structural formula (I).

A method of inhibiting glucosylceramide synthase or lowering glycosphingolipid concentrations in a subject in need thereof also is included in the present invention. The method comprises administering to the subject a therapeutically effective amount of a compound of structural formula (I).

The present invention also is directed to a method of treating a glomerular disease selected from the group consisting of mesangial proliferative glomerulonephritis, collapsing glomerulopathy, proliferative lupus nephritis, crescentic glomerulonephritis, and membranous nephropathy in a subject, comprising administering to the subject a therapeutically effective amount of a compound of structural formula (I).

In another embodiment, the invention is directed to a method of treating lupus in a subject comprising administering to the subject a therapeutically effective amount of a compound of structural formula (I).

In yet another embodiment, in the treatment of the above disclosed diseases, a compound of structural formula (I) can be administered on the sole therapeutic agent or in combination with a second therapeutic agent known to treat the disease of interest.

Another embodiment of the present invention is to provide a composition comprising (a) a GCS inhibitor of structural formula (I) and (b) an excipient and/or pharmaceutically acceptable carrier useful in treating diseases or conditions wherein inhibition of GCS provides a benefit.

Another embodiment of the present invention is to utilize a composition comprising a compound of structural formula (I) and a second therapeutically active agent in a method of treating an individual for a disease or condition wherein inhibition of GCS provides a benefit.

In a further embodiment, the invention provides for use of a composition comprising a GCS inhibitor of structural formula (I) and an optional second therapeutic agent for the manufacture of a medicament for treating a disease or condition of interest, e.g., Gaucher disease or Fabry disease.

Still another embodiment of the present invention is to provide a kit for human pharmaceutical use comprising (a) a container, (b1) a packaged composition comprising a GCS inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The GCS inhibitor of structural formula (I) and the second therapeutic agent can be administered together as a single-unit dose or separately as multi-unit doses, wherein the GCS inhibitor of structural formula (I) is administered before the second therapeutic agent or vice versa. It is envisioned that one or more dose of a GCS inhibitor of structural formula (I) and/or one or more dose of a second therapeutic agent can be administered.

In one embodiment, a GCS inhibitor of structural formula (I) and a second therapeutic agent are administered simultaneously. In related embodiments, a GCS inhibitor of structural formula (I) and second therapeutic agent are administered from a single composition or from separate compositions. In a further embodiment, the GCS inhibitor of structural formula (I) and second therapeutic agent are administered sequentially. A GCS inhibitor of structural formula (I), as used in the present invention, can be administered in an amount of about 0.005 to about 500 milligrams per dose, about 0.05 to about 250 milligrams per dose, or about 0.5 to about 100 milligrams per dose.

Compounds of the invention inhibit GCS and are useful research tools for in vitro study of GCS and its role in biological process.

These and other novel aspects of the present invention will become apparent from the following detailed description of the present embodiments.

DETAILED DESCRIPTION OF THE PREFERRED EMBODIMENTS

Figure 1:
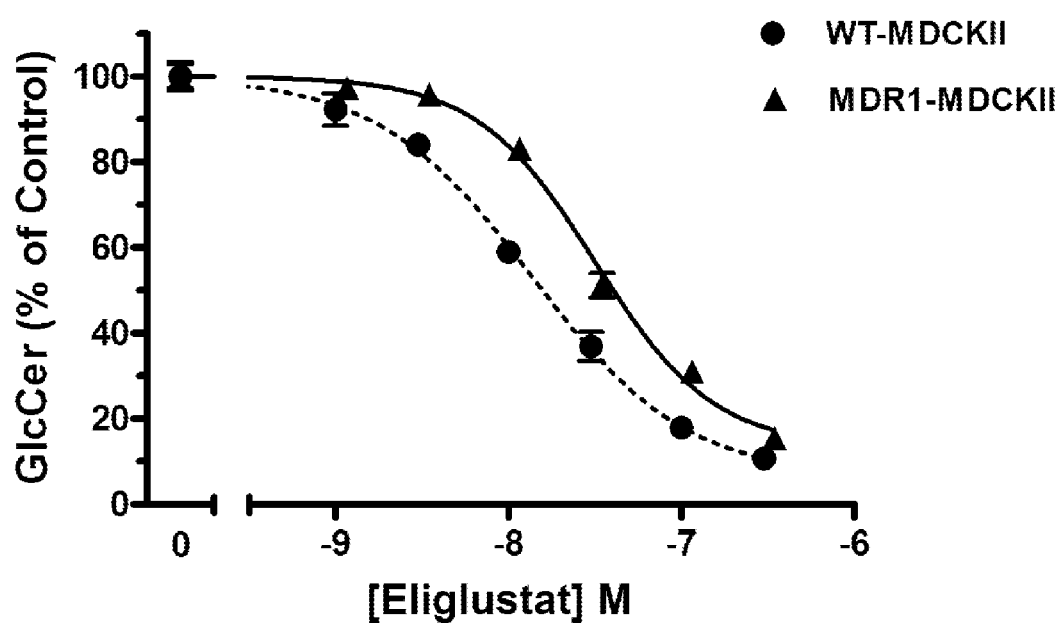
FIG. 1 is a graph of GlcCer (% of control) in WT-MDCK11 and MDR 1-MD CK11 cells vs. eliglustat concentration.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "GCS" as used herein means glucosylceramide synthase.

The term "a disease or condition wherein inhibition of GCS provides a benefit" pertains to a condition in which GCS, and/or an action of GCS, is important or necessary, e.g., for the onset, progress, expression of that disease or condition, or a disease or a condition which is known to be treated by a GCS inhibitor (such as eliglustat tartrate). An example of such a condition includes, but is not limited to, Gaucher disease and Fabry disease. One of ordinary skill in the art is readily able to determine whether a compound treats a disease or condition mediated by GCS, for example, by assays which conveniently can be used to assess the activity of particular compounds.

The term "second therapeutic agent" refers to a therapeutic agent different from a GCS inhibitor of structural formula (I) and that is known to treat the disease or condition of interest. For example when Gaucher disease is the disease or condition of interest, the second therapeutic agent can be a known for the treatment of type (I) Gaucher disease or Fabry disease, like isofagomine, enzyme replacement therapy, or gene therapy for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a compound of structural formula (I) is an inhibitor of GCS and can be used in treating diseases and conditions wherein inhibition of GCS provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active agent(s) that is(are) sufficient, when administered by a method of the invention, to efficaciously deliver the active agent(s) for the treatment of condition or disease of interest to an individual in need thereof. In the case of a lysosomal storage disorder, the therapeutically effective amount of the agent may reduce (i.e., retard to some extent and preferably stop) unwanted glycolipid accumulation and/or relieve, to some extent, one or more of the symptoms associated with the disorder.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a GCS inhibitor of structural formula (I) can be administered at the same time or sequentially in any order at different points in time as a second therapeutic agent. A present GCS inhibitor and the second therapeutic agent can be administered separately, in any appropriate form and by any suitable route. When a present GCS inhibitor and the second therapeutic agent are not administered concurrently, it is understood that they can be administered in any order to a subject in need thereof.

For example, a present GCS inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a GCS inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Compounds that inhibit glycolipid synthesis are known. As such, these compounds can be used for treating diabetes and lysosomal storage diseases, such as Tay-Sachs disease, Sandhoff disease, Gaucher disease, and Fabry disease. However, to date, these compounds have been limited by low activity, poor CNS penetration, or both.

For example, glycolipid synthesis inhibition is the basis for the treatment of type 1 Gaucher disease by the glucosylceramide (GCS) inhibitor eliglustat tartrate. However, the use of eliglustat for the treatment of glycosphingolipid storage diseases with CNS manifestations is limited by the lack of brain penetration of this drug.

Recent Phase 2 clinical data for eliglustat tartrate demonstrated a clinical response in type 1 Gaucher disease that is comparable to enzyme replacement therapy, as measured by reduction in spleen and liver volume, correction of anemia, and improvement in thrombocytopenia. The adverse effects observed with NBDNJ, including weight loss, diarrhea, and tremor, were not observed in this clinical trial, as well as in an extension study. These observations are consistent with the high specificity of eliglustat tartrate and its absence of CNS penetration. While the absence of eliglustat tartrate distribution into brain may be advantageous for glycosphingolipi-doses without CNS manifestations, including type 1 Gaucher and Fabry diseases, the identification of compounds of structural formula (I) that cross the BBB is of therapeutic benefit for disorders such as GM2 gangliosidoses, Tay-Sachs, Sandhoff disease, and types 2 and 3 Gaucher disease, that exhibit CNS manifestations.

The GCS inhibitors of the present invention are novel and potent inhibitors of GCS, and therefore are useful in the treatment of diseases and conditions resulting from an unwanted accumulation of glycolipids, including Gaucher disease and type II diabetes. Also provided are methods of treating a subject having an unwanted accumulation of glycolipids comprising administering a therapeutically effective amount of a present compound to a subject in need of such treatment.

Also provided are methods of preventing the proliferation of unwanted glycolipid accumulation in a subject comprising the step of administering a therapeutically effective amount of a compound of structural formula (I) to a subject at risk of developing a condition characterized by unwanted glycolipid accumulation. In some embodiments, compounds of structural formula (I) are capable of crossing the BBB, therefore are useful in the treatment of lysosomal storage diseases that previously could not be treated by a GCS inhibitor, for example, type II and type III Gaucher disease.

More particularly, the present invention is directed to compounds having a structural formula (I):

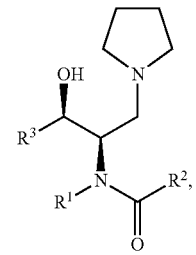

(I)

wherein $R^1$ is H or $C_{1-3}$alkyl;

$R^2$ is (i) —$(CH_2)_{1-3}C_6H_5$, with the proviso that $R^1$ is —$C_{1-3}$alkyl, (ii) —$CH_2$—$C(R^a{}_2)_{1,2}$—$C_6H_5$ wherein $R^a$ independently is H or $C_{1-3}$alkyl, with the proviso that at least one $R^a$ is $C_{1-3}$alkyl,

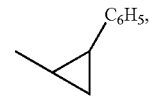

(iii)

—$CH$=$CHC_6H_5$, (iv)

(v)

wherein for (i) through (v) the $C_6H_5$ group optionally is substituted with one or two of -halo or —$OR^a$, or

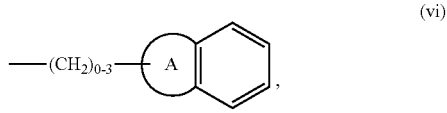

(vi)

wherein the fused ring A is a 4- to 8-membered ring, saturated or partially unsaturated, and comprising carbon atoms and optionally one or two heteroatoms selected from O, S, and NR$^a$, and wherein the fused phenyl ring is optionally substituted with one or two substituents; and R$^3$ is

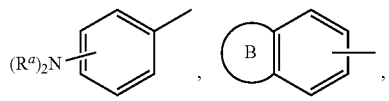

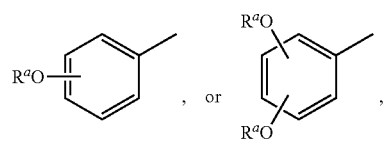

wherein the fused ring B is a five- or six-membered ring, saturated or partially or fully unsaturated, comprising carbon atoms and one or two heteroatoms selected from O, S, and NR$^a$, and wherein the phenyl ring is optionally substituted with one or two substitutents;

or a pharmaceutically acceptable salt, hydrate, solvate, or prodrug thereof.

The compounds of structural formula (I) are used in methods of treating a disease or condition wherein inhibition of GCS provides a benefit, for example Gaucher disease, Fabry disease, Tay-Sachs disease, Sandhoff disease, diabetes, hypertrophy or hyperplasia associated with diabetic neuropathy, lupus, increased plasma TNF-α, elevated glycated hemoglobin levels, and a glomerular disease. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof.

As used herein, the term "alkyl" refers to straight chained and branched saturated hydrocarbon groups, nonlimiting examples of which include methyl, ethyl, and straight chain and branched propyl, butyl, pentyl, and hexyl groups. The term "C$_{x-y}$alkyl" means the alkyl group contains from x to y carbon atoms.

The term "alkenyl" is defined identically as "alkyl," except for containing a carbon-carbon double bond, e.g., ethenyl, propenyl, and butenyl.

As used herein, the term "halo" means fluoro, chloro, bromo, and iodo.

As used herein, (CH$_3$)$_2$N is an abbreviation for (CH$_3$)$_2$NH.

As used herein, —CH=CHC$_6$H$_5$ means

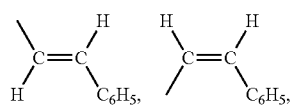

or a mixture thereof.

As used herein,

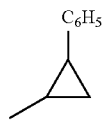

means

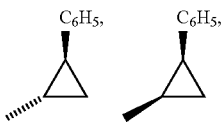

or a mixture thereof.

As used herein, the term "aryl" refers to a monocyclic or polycyclic aromatic group, preferably a monocyclic or bicyclic aromatic group, e.g., phenyl (C$_6$H$_5$) and naphthyl. Unless otherwise indicated, an aryl group, e.g., a phenyl (C$_6$H$_5$), group can be either unsubstituted or substituted with one or more, and in particular one or two, groups independently selected from, for example, halo, alkyl, alkenyl, C$_{3-8}$cycloalkyl, heterocycloalkyl, —OCF$_3$, —NO$_2$, —CN, —NC, —OH, alkoxy (—Oalkyl), amino (—NR$^2$, wherein each R, independently, is hydrogen, alkyl, aryl, or heteroaryl), —CO$_2$H, —CO$_2$alkyl, aryl, and heteroaryl. Exemplary substituted phenyl groups include, but are not limited to, tetrahydronaphthyl, chlorophenyl, fluorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be either unsubstituted or substituted with one or more, and in particular one to three, substituents selected from, for example, halo, alkyl, alkenyl, C$_{3-8}$cycloalkyl, heterocycloalkyl, —OCF$_3$, NO$_2$, —CN, —NC, —OH, alkoxy, amino, —CO$_2$H, —CO$_2$alkyl, aryl, and heteroaryl. Examples of heteroaryl groups include, but are not limited to, thienyl, furyl, oxazolyl, quinolyl, thiophenyl, isoquinolyl, indolyl, triazinyl, triazolyl, isothiazolyl, isoxazolyl, imidazolyl, benzothiazolyl, pyrimidinyl, thiazolyl, thiadiazolyl, pyridinyl, pyridazinyl, pyrazolyl, pyrazinyl, quinolyl, tetrazolyl, oxazolyl, pyrrolyl, benzimidazolyl, benzofuranyl, cinnolinyl, indazolyl, indolizinyl, phthalazinyl, triazinyl, isoindolyl, purinyl, oxadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, napththyridinyl, dihydroquinolyl, tetrahydroquinolyl, dihydroisoquinolyl, tetrahydroisoquinolyl, benzofuryl, furopyridinyl, pyrrolopyrimidinyl, and azaindolyl.

As used herein, the term "C$_{3-8}$cycloalkyl" means a monocyclic aliphatic ring containing three to eight carbon atoms.

As used herein, the term "heterocycloalkyl" means a monocyclic or a bicyclic aliphatic ring containing 5 to 10 total atoms, of which one to five of the atoms are independently selected from nitrogen, oxygen, and sulfur and the remaining atoms are carbon.

In various embodiments, $R^1$ is H, —CH$_3$, —CH$_2$CH$_3$, —CH$_2$CH$_2$CH$_3$, or

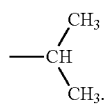

In preferred embodiments, $R^1$ is H or —CH$_3$.

In various embodiments, $R^2$ is —CH$_2$C$_6$H$_5$, —CH$_2$CH$_2$C$_6$H$_5$, or —CH$_2$CH$_2$CH$_2$C$_6$H$_5$, when $R^1$ is —CH$_3$, —CH$_2$CH$_3$, —CH$_2$CH$_2$CH$_3$, or

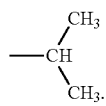

In other embodiments, $R^2$ is —CH$_2$—C(R$^a$)$_2$—C$_6$H$_5$ or —CH$_2$—C(R$^a$)$_2$—C(R$^a$)$_2$—C$_6$H$_5$, wherein $R^a$ independently is H, —CH$_3$, —CH$_2$CH$_3$, —CH$_2$CH$_2$CH$_3$, or

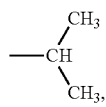

and wherein at least one $R^a$ is different from H.

In still other embodiments, $R^2$ is —CH$_2$NHC$_6$H$_5$ or —CH$_2$CH$_2$NC$_6$H$_5$. In additional embodiments, $R^2$ is

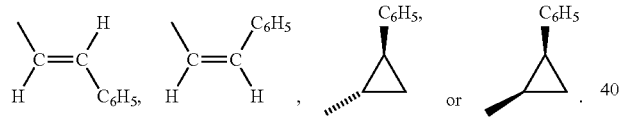

In each of the above embodiments, the phenyl (C$_6$H$_5$) substitutent of the $R^2$ group can be substituted with one or two of —F, —Cl, —Br, —I, —OH, or —OR$^a$, wherein $R^a$ is —CH$_3$, —CH$_2$CH$_3$, —CH$_2$CH$_2$CH$_3$, or

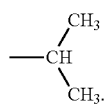

In preferred embodiments, the phenyl substituent is substituted with one or two of —Cl, —F, or —OCH$_3$.

In other embodiments, $R^2$ is

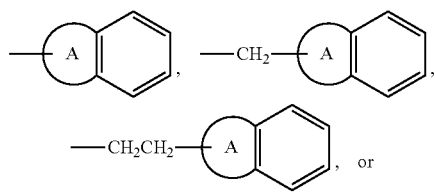

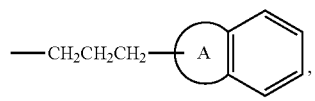

and the A ring is selected from the group consisting of

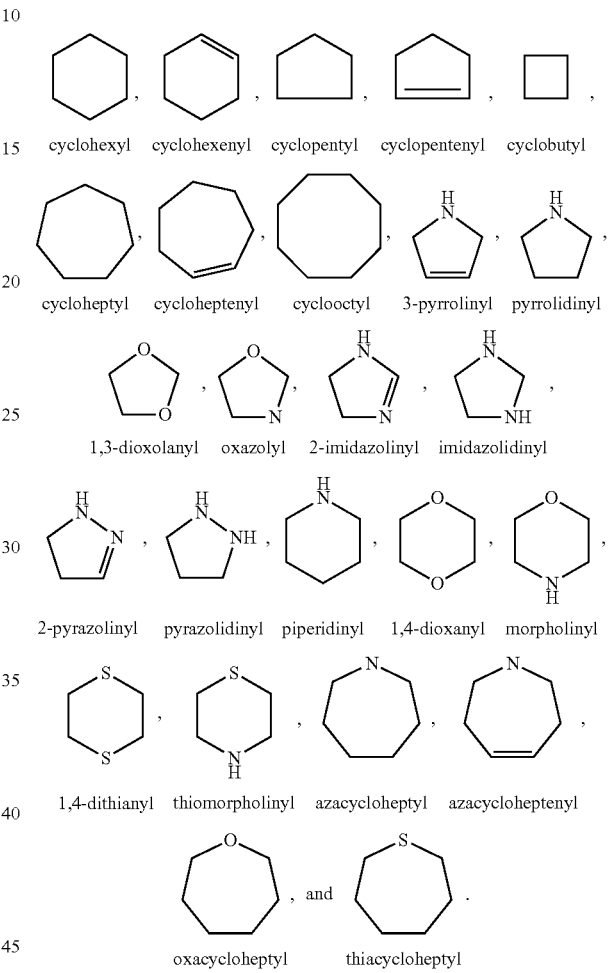

In each of the above ring systems, the hydrogen of an aliphatic nitrogen atom can be replaced by C$_{1-3}$alkyl.

The above A rings can be attached to the phenyl ring of the bicyclic structure in any possible orientation, for example, piperidinyl can be bonded to the phenyl of the bicyclic ring system in any of the following orientations:

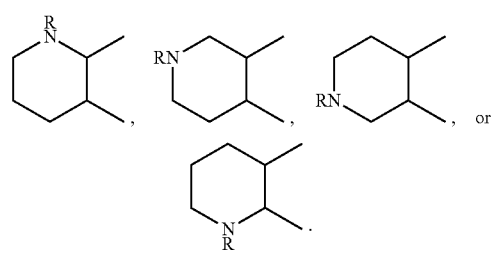

In some preferred embodiments of $R^2$,

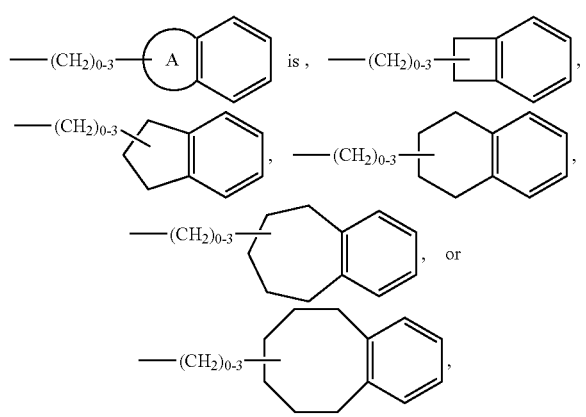

In one preferred embodiment $R^2$ is

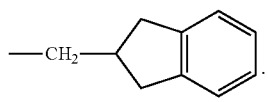

In embodiments of $R^3$, $R^a$ is H, —CH$_3$, —CH$_2$CH$_3$, —CH$_2$CH$_2$CH$_3$, or

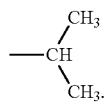

In some embodiments of $R^3$, the fused B ring is selected from the group consisting of

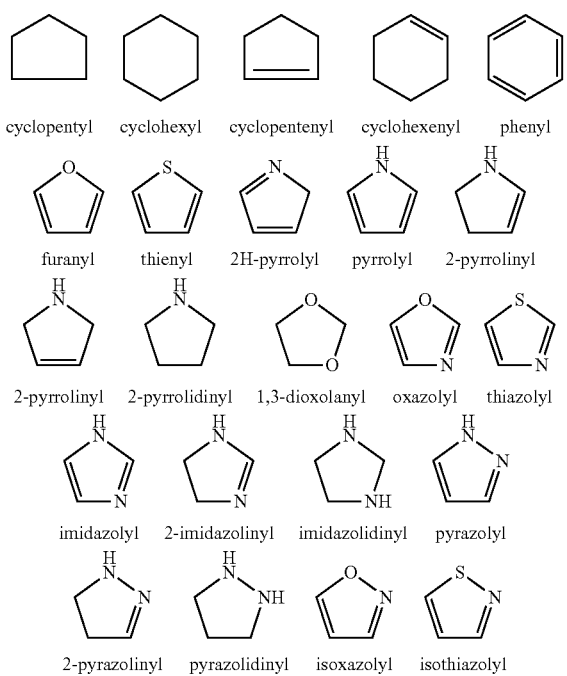

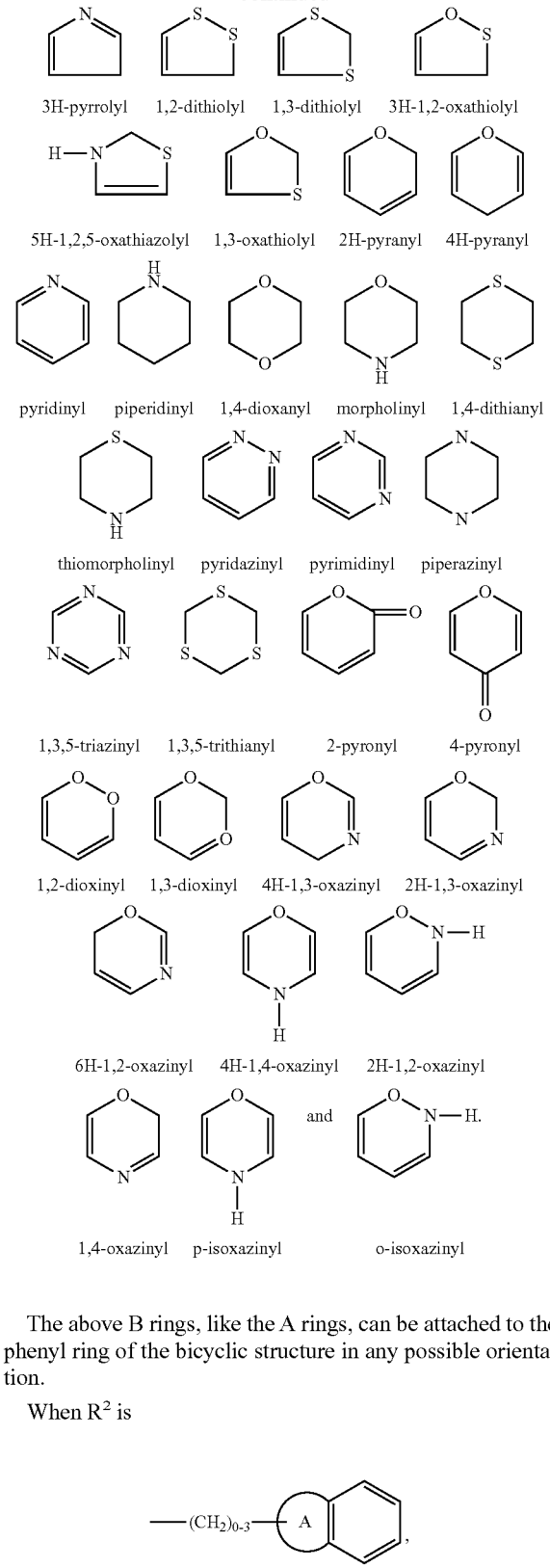

The above B rings, like the A rings, can be attached to the phenyl ring of the bicyclic structure in any possible orientation.

When $R^2$ is

—(CH$_2$)$_{0-3}$—(A)— the fused phenyl rings, and for the phenyl rings of $R^3$, the phenyl ring can be substituted with one or two substituents, for example, but not limited to, halo, C$_{1-6}$alkyl, C$_{2-6}$alkenyl, aryl, heteroaryl, cycloalkyl, heterocycloalkyl, nitro, trifluoromethyl, trifluoromethoxy, cyano, $SO_2N(R^a)_2$, $SO_2R^a$, $SOR^a$, $SR^a$, and $OSO_2CF_3$.

In one preferred embodiment, $R^3$ is

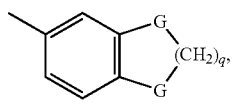

wherein q is an integer 1 or 2, and G, independently, is O, S, or $NR^a$. In an especially preferred group, $R^3$ is represented by an optionally substituted bicyclic ring

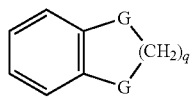

wherein q is 1 or 2, and G is O, for example,

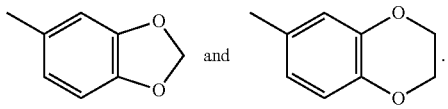

Within this group of compounds, nonlimiting examples of substitutents for the phenyl ring include, but are not limited to halo (e.g., chloro), $C_{1-3}$alkyl (e.g., methyl, ethyl, or i-propyl), $OR^a$, $CO_2R^a$, halomethyl, or halomethoxy (e.g., trifluoromethyl or trifluoromethoxy), cyano, nitro, and $N(R^a)_2$.

Additional nonlimiting examples of $R^3$ are

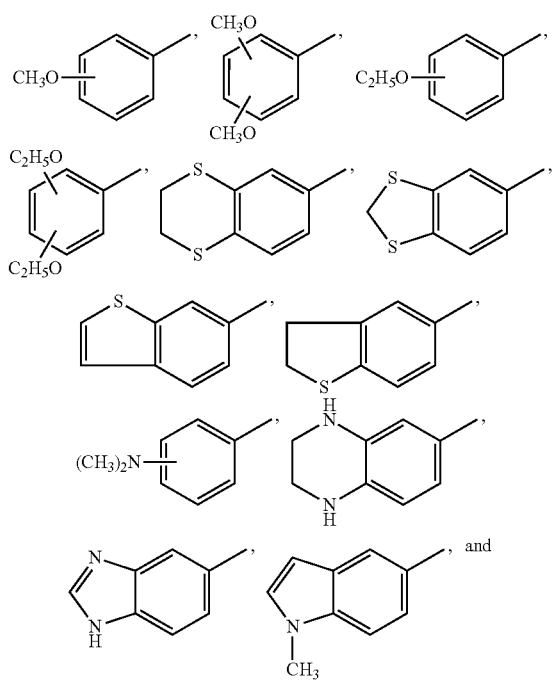

Additionally, salts, hydrates, solvates, and prodrugs of the present compounds also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, glutarate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or solvates thereof.

Prodrugs of compounds of structural formula (I) also are included in the present invention. It is well established that a prodrug approach, wherein a compound is derivatized into a form suitable for formulation and/or administration, then released as a drug in vivo, has been successfully employed to transiently (e.g., bioreversibly) alter the physiochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., *Med. Res. Rev.*, 15, 83 (1995)).

Some specific embodiments of the present invention include, but are not limited to:

Compound 3f

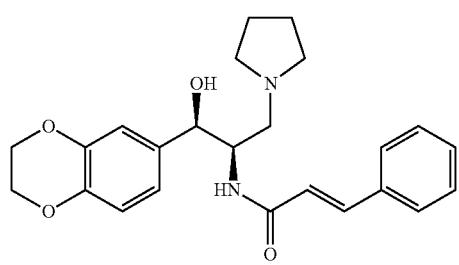

N-((1R,2R)-1-(2,3-dihydrobenzo[b][1,4]dioxin-6-yl)-1-hydroxy-3-(pyrrolidin-1-yl)propan-2-yl)cinnamamide Compound 3g

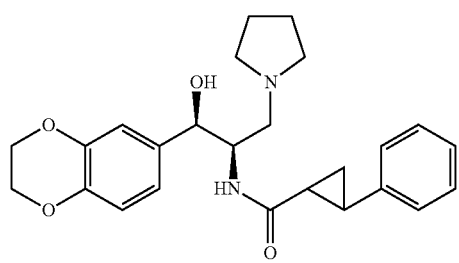

N-((1R,2R)-1-(2,3-dihydrobenzo[b][1,4]dioxin-6-yl)-1-hydroxy-3-(pyrrolidin-1-yl)propan-2-yl)-2-phenylcyclopropanecarboxamide Compound 3h

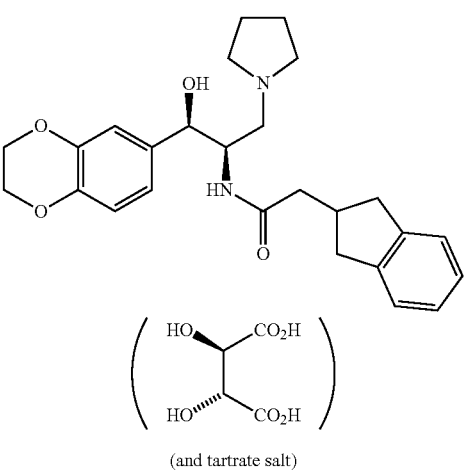

2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide Compound 3i

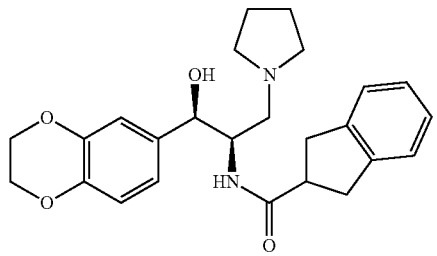

N-((1R,2R)-1-(2,3-dihydrobenzo[b][1,4]dioxin-6-yl)-1-hydroxy-3-(pyrrolidin-1-yl)propan-2-yl)-2,3-dihydro-1H-indene-2-carboxamide Compound 3j

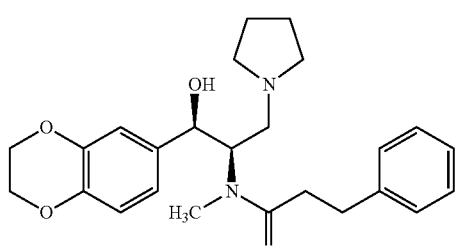

(1R,2R)-2-amino-1-(2-methoxyphenyl)-3-(pyrrolidin-1-yl)propan-1-ol

Compound 7

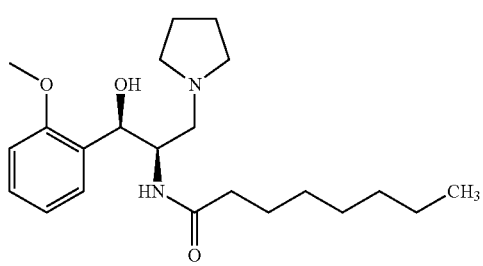

N-((1R,2R)-1-hydroxy-1-(2-methoxyphenyl)-3-(pyrrolidin-1-yl)propan-2-yl)octanamide. 25

Compound 8

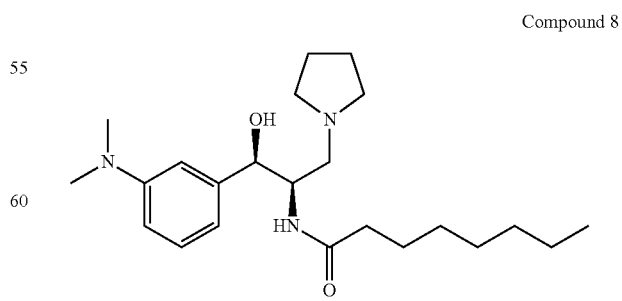

N-((1R,2R)-1-(3-(dimethylamino)phenyl)-1-hydroxy-3-(pyrrolidin-1-yl)propan-2-yl)octanamide Compound 9

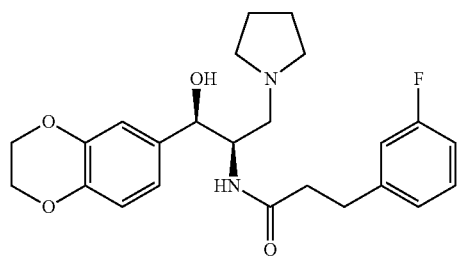

N-((1R,2R)-1-(2,3-dihydrobenzo[b][1,4]dioxin-6-yl)-1-hydroxy-3-(pyrrolidin-1-yl)propan-2-yl)-3-(3-fluorophenyl)propanamide Compound 10

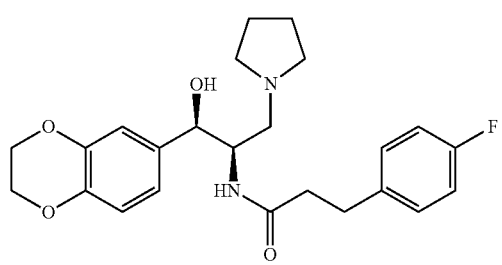

N-((1R,2R)-1-(2,3-dihydrobenzo[b][1,4]dioxin-6-yl)-1-hydroxy-3-(pyrrolidin-1-yl)propan-2-yl)-3-(4-fluorophenyl)propanamide Compound 11

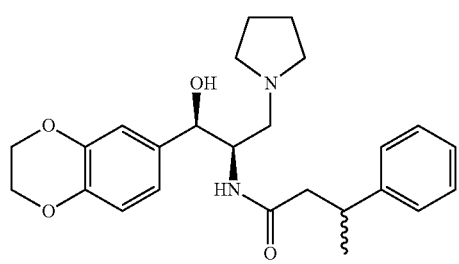

N-((1R,2R)-1-(2,3-dihydrobenzo[b][1,4]dioxin-6-yl)-1-hydroxy-3-(pyrrolidin-1-yl)propan-2-yl)-3-phenylbutanamide (mixture of diastereomers)

Compound 12

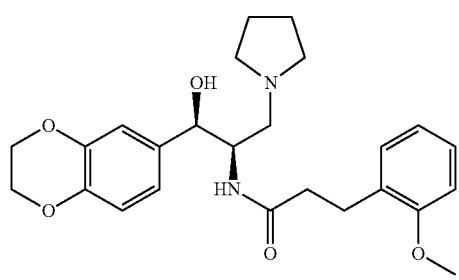

N-((1R,2R)-1-(2,3-dihydrobenzo[b][1,4]dioxin-6-yl)-1-hydroxy-3-(pyrrolidin-1-yl)propan-2-yl)-3-(2-methoxyphenyl)propanamide Compound 13

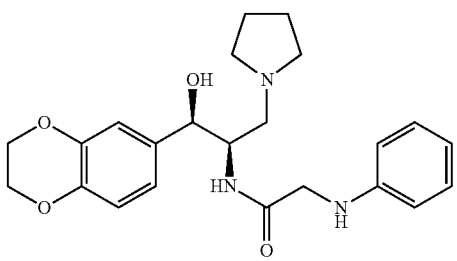

N-((1R,2R)-1-(2,3-dihydrobenzo[b][1,4]dioxin-6-yl)-1-hydroxy-3-(pyrrolidin-1-yl)propan-2-yl)-2-(phenylamino)acetamide Compound 14

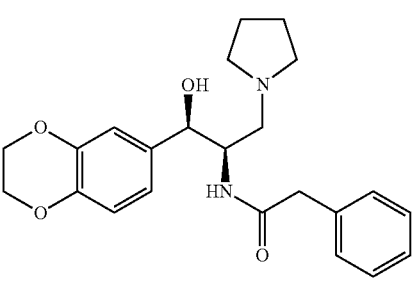

2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide oxylate monohydrate Compound 15

N-((1R,2R)-1-(2,3-dihydrobenzo[b][1,4]dioxin-6-yl)-1-hydroxy-3-(pyrrolidin-1-yl)propan-2-yl)-2-phenylacetamido

SYNTHESIS OF COMPOUNDS

Compounds of the present invention were prepared as follows. The following synthetic schemes are representative of the reactions used to synthesize compounds of structural formula (I). Modifications and alternate schemes to prepare GCS inhibitors of the invention are readily within the capabilities of persons skilled in the art.

General Synthetic Schemes for the Preparation of Compounds of Structural Formula (I)

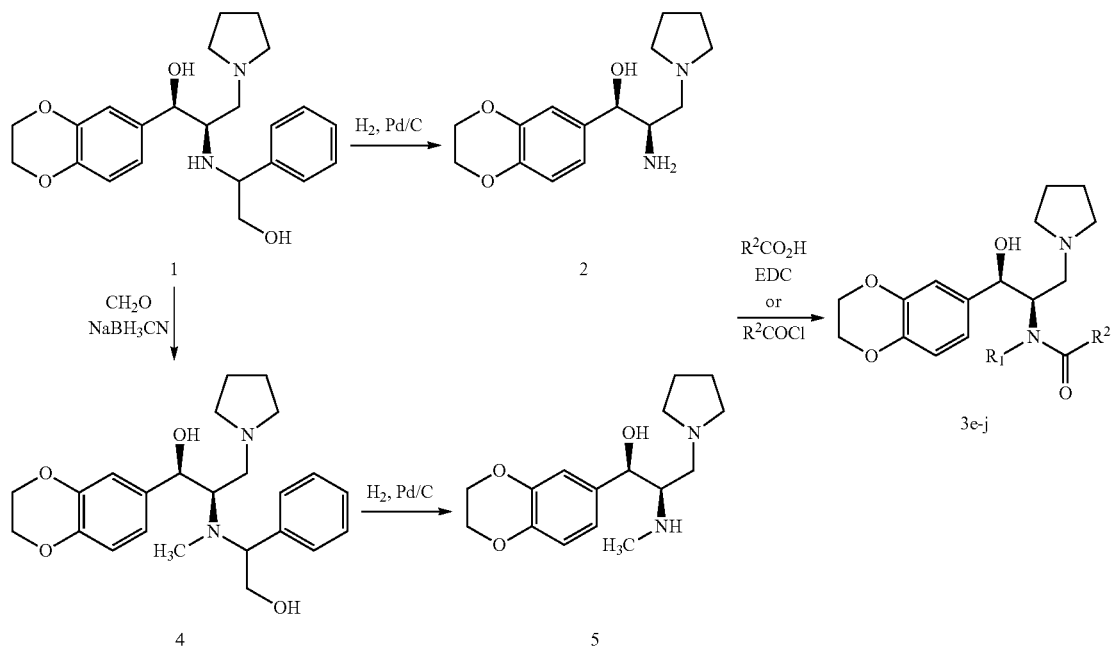

Preparation and Spectroscopic Data of the GSC Compounds of Structural Formula (I)

Chemical names follow CAS nomenclature. Starting materials were purchased from Fisher, Sigma-Aldrich Lancaster, Fluka, or TCI-America, and were used without purification. All reaction solvents were purchased from Fisher and used as received. Reactions were monitored by TLC using pre-coated silica gel 60 F254 plates. Silica gel chromatography was performed with silica gel (220-240 mesh) obtained from Silicycle.

NMR spectra were recorded on a Bruker 500 MHz spectrometer. Chemical shifts are reported in δ (parts per million) by reference to the hydrogenated residues of deuterated solvent as internal standard $CDCL_3$: δ=7.28 ($^1$H NMR). Mass spectra were recorded on a Micromass LCT time-of-flight instrument utilizing the positive electrospray ionization mode. The purity of the compounds was assessed via analytical reverse phase HPLC with a gradient of 10-90% $CH_3CN$/water over 6 minutes (Agilent Eclipse Plus C18 4.6×75 mm column (3.5 μm silica), 254 nm detection).

Unless otherwise stated all temperatures are in degrees Celsius.

In these examples and elsewhere, abbreviations have the following meanings:
NMR=proton nuclear magnetic resonance
$CH_3CN$=acetonitrile
aq.=aqueous
$CDCl_3$=deuterated chloroform
d=doublet
$CH_2Cl_2$=dichloromethane
DMF=dimethylformamide
$CH_2O$=paraformaldehyde
EDC=1-(3-dimethylaminopropyl)-3-ethylcarbodiimide)
EDTA=ethylenediaminetetraacetic acid
ESI=electro spray ionization
EtOAc=ethyl acetate
FBS=fetal bovine serum
g=grams
GlcCer=glucosyl ceramide
h=hours
HCl=hydrochloric acid
$H_2$=hydrogen gas
HEPES=4-(2-hydroxyethyl)-1-piperazineethanesulfonic acid
HOBT=1-hydroxybenzotriazole
HPLC=high performance liquid chromatography
m=multiplet
mg=milligrams
MeOH=methanol
$MgSO_4$=magnesium sulfate
MHz=megahertz
min=minutes
mL=milliliters
mM=millimolar
mmol=millimole
ESI-MS=mass spectrometry (electrospray ionization)
N=normal
nm=nanomolar
$N_2$=nitrogen gas
$NH_3$=ammonia
$NaBH_3CN$=sodium cyanoborohydride
$NaHCO_3$=sodium bicarbonate
NaCl=sodium chloride
NaOH=sodium hydroxide
Pd/C or Pd on C=palladium on carbon
PBS=phosphate buffered saline
psi=pounds per square inch
$t_R$=retention time
rt or RT=room temperature
s=singlet
satd.=saturated
t=triplet THF=tetrahydrofuran
mg=microgram
μL=microliter
μmol=micromolar
U/mL=units per milliliter
UV=ultraviolet
v=volume
δ=chemical shift Compound 2

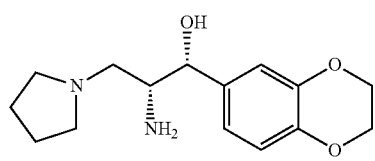

(1R,2R)-2-amino-1-(2,3-dihydrobenzo[b][1,4]dioxin-6-yl)-3-(pyrrolidin-1-yl)propan-1-ol (2). Prepared from compound 1 in above general scheme as disclosed in U.S. Pat. No. 6,855,830, incorporated herein by reference.

Compound 4

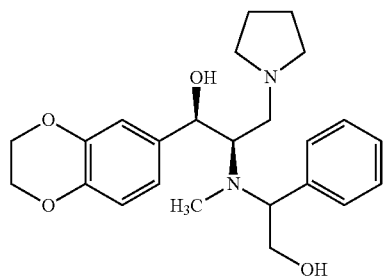

(1R,2R)-1-(2,3-dihydrobenzo[b][1,4]dioxin-6-yl)-2-((2-hydroxy-1-phenylethyl)(methyl)amino)-3-(pyrrolidin-1-yl)propan-1-ol (4). To a solution of compound 1 (U.S. Pat. No. 6,855,830, 0.65 g, 1.4 mmol) in methanol (8 mL) was added paraformaldehyde (0.051 g, 1.71 mmol). The resulting mixture was stirred overnight at room temperature, treated with sodium cyanoborohydride (0.089 g, 1.42 mmol) and allowed to stir overnight at room temperature. The mixture was concentrated and purified by flash chromatography (MeOH/CH$_2$Cl$_2$), providing compound 4 as a clear oil (0.20 g, 0.425 mmol, 30%). HPLC purity: 89% ($t_R$=4.52 min). The compound was used without further purification.

Compound 5

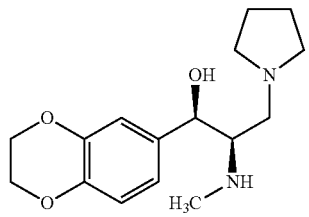

(1R,2R)-1-(2,3-dihydrobenzo[b][1,4]dioxin-6-yl)-2-(methylamino)-3-(pyrrolidin-1-yl)propan-1-ol (5). To a solution of compound 4 (0.22 g, 0.468 mmol) in methanol 20 mL and 1 N HCl (5 mL) was added palladium (10%) on carbon (0.08 g, 0.752 mmol) (Degussa wet catalyst). The flask was attached to a Parr 3911 hydrogenation apparatus, evacuated via a water aspirator, and filled with H$_2$ (40 psi). After shaking for 18 hours at room temperature, the mixture was filtered through celite with MeOH eluent. The celite pad then was washed with methanol (2×) and 2 M NH$_3$ in dioxane (2×). The filtrate was concentrated, diluted with water, and washed with EtOAc (1×). The aq layer was made basic with satd. aq. NaHCO$_3$ and extracted with CH$_2$Cl$_2$ (2×) and EtOAc (3×). The combined layers were dried over MgSO$_4$, concentrated to an oil, and used without further purification. HPLC purity 89% ($t_R$=4.88 min). NMR (500 MHz, CDCl$_3$) δ 6.9 (s, 1H), 6.7-6.8 (m, 2H), 4.6 (d, 1H), 4.3 (s, 4H), 2.8-2.9 (m, 1H), 2.4-2.5 (m, 6H), 2.4 (m, 3H), 1.7-1.8 (m, 5H). ESI-MS m/z 293.1 (M+H$^+$).

Compound 3f

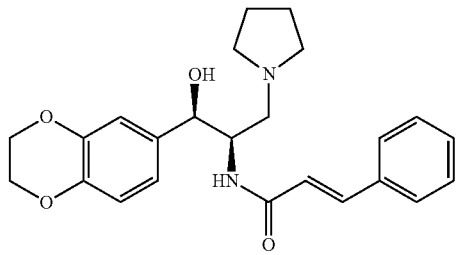

N-((1R,2R)-1-(2,3-dihydrobenzo[b][1,4]dioxin-6-yl)-1-hydroxy-3-(pyrrolidin-1-yl)propan-2-yl)cinnamamide (3f). To a 0° C. solution of compound 2 (0.2 g, 0.72 mmol) in THF (4 mL) was added Hunig's Base (0.09 g, 0.72 mmol), followed by cinnamoyl chloride (0.11 g, 0.72 mmol) dropwise. The resulting mixture was allowed to stir overnight at room temperature. The resulting mixture was allowed to stir overnight at room temperature, diluted with EtOAc, and washed with satd. aq. NaHCO$_3$, satd. aq. NaCl, and dried over MgSO$_4$. Purification by flash silica chromatography (MeOH/CH$_2$Cl$_2$) gave a yellow oil (0.13 g, 0.32 mmol, 43% yield). HPLC purity 91% ($t_R$=5.28 min). NMR (500 MHz, CDCl$_3$) δ 7.6-7.4 (m, 6H), 6.8-6.9 (m, 3H), 6.4 (d, 1H, J=7.8), 6.0-6.1 (m, 1H), 5.0 (s, 1H), 4.3-4.4 (m, 5H), 2.7-2.9 (m, 2H), 2.6-2.7 (m, 4H), 1.67-1.8 (m, 4H). ESI-MS m/z 409.2 (M+H$^+$).

Compound 3g

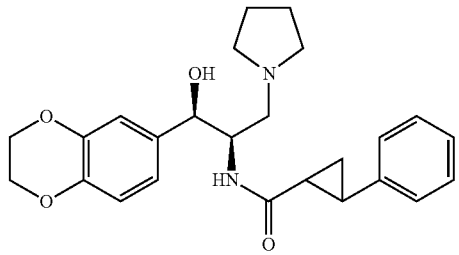

N-((1R,2R)-1-(2,3-dihydrobenzo[b][1,4]dioxin-6-yl)-1-hydroxy-3-(pyrrolidin-1-yl)propan-2-yl)-2-phenylcyclopropanecarboxamide (3g). To a 0° C. solution of compound 2 (0.2 g, 0.719 mmol) in THF (4 mL) was added Hunig's Base (0.093 g, 0.719 mmol) followed by racemic E-2-phenylcyclopropanecarbonyl chloride (0.11 g, 0.72 mmol) dropwise. The resulting mixture was allowed to stir overnight at room temperature, diluted with EtOAc, and washed with satd. aq. NaHCO$_3$, satd. aq. NaCl, and dried over MgSO$_4$. Purification by flash silica chromatography (MeOH/CH$_2$Cl$_2$) gave a yellow oil (0.11 g, 0.24 mmol, 26.4% yield). HPLC purity 96% ($t_R$=4.36 min). NMR (500 MHz, CDCl 3) δ 7.0-7.4 (m, 6H), 6.7-6.9 (m, 3H), 5.1-5.2 (s, 1H), 4.3-4.4 (m, 5H), 3.8-3.9 (m, 1H), 3.4-3.5 (m, 1H), 2.8-3.1 (m, 1H), 2.0-2.5 (m, 5H) 1.5-1.8 (m, 5H), 1.1-1.3 (m, 1H). ESI-MS m/z 423.1 (M+H$^+$).

Compound 3h

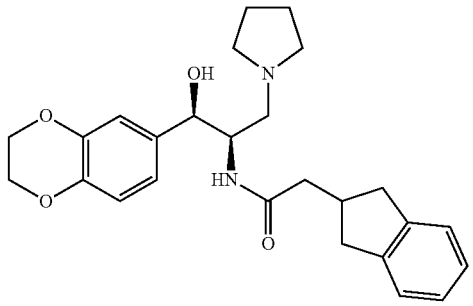

2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide. To a solution of compound 2 (0.1 g, 0.36 mmol) in DMF 5 mL was added 2-(2,3-dihydro-1H-inden-2-yl)acetic acid (0.063 g, 0.36 mmol), HOBt (0.063 g, 0.47 mmol), and EDC (0.10 g, 0.54 mmol) followed by Hunig's base (0.14 mL, 0.83 mmol). The resulting mixture was stirred overnight at room temperature before addition of satd. aq. NaHCO$_3$ and EtOAc. The separated aq layer was extracted again with ethyl acetate. The combined organic layers were washed with satd. aq. NaCl (3×) and dried (MgSO$_4$). Purification by flash chromatography (MeOH/CH$_2$Cl$_2$) gave an oil (0.045 g, 0.10 mmol, 29% yield). HPLC purity 95% ($t_R$=5.24 min). NMR (500 MHz, CDCl$_3$) δ 6.9-7.1 (m, 4H), 6.8-6.9 (m, 3H), 6.0 (s, 1H), 4.9 (s, 1H), 4.2-4.3 (m, 5H), 2.9-3.0 (m, 4H), 2.6-2.7 (m, 5H), 2.5-2.6 (m, 1H), 2.4-2.5 (m, 2H) 2.2-2.4 (m, 2H), 2.2 (s, 4H). ESI-MS m/z 437.1 (M+H$^+$).

Compound 3h

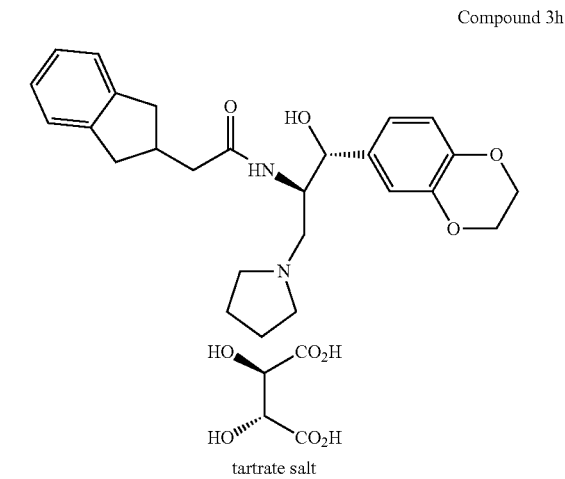

tartrate salt

To a solution of 2-(2,3-dihydro-1H-inden-2-yl)-N-((1R)-1-(2,3-dihydrobenzo[b][1,4]dioxin-6-yl)-1-hydroxy-3-(pyrrolidin-1-yl)propan-2-yl)acetamide (compound 3h) (0.15 g, 0.34 mmol) in isopropanol (10 ml) was added a solution of (+)-tartaric acid (0.05 g, 0.34 mmol) in MeOH (5 mL). The resulting mixture was stirred 30 minutes, then concentrated in vacuo. EtOAc was added followed by diethyl ether (excess). The resulting solid was stirred 30 minutes, then allowed to set overnight. The solid was filtered, washed with diethyl ether, and dried overnight under high vacuum to yield 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide tartrate, 0.16 g, 79% desired white solid. ESI-MS m/z 437.2 (M+H$^+$). mp=174-175° C.

Compound 3i

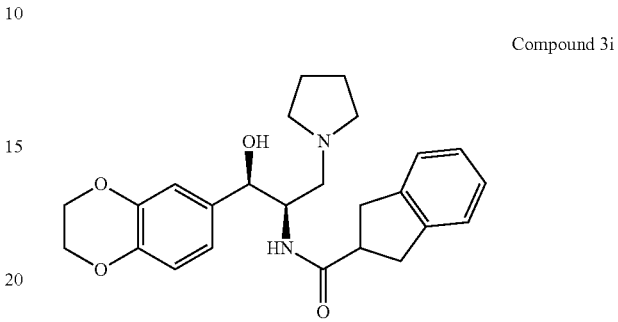

N-((1R,2R)-1-(2,3-dihydrobenzo[b][1,4]dioxin-6-yl)-1-hydroxy-3-(pyrrolidin-1-yl)propan-2-yl)-2,3-dihydro-1H-indene-2-carboxamide. To a solution of compound 2 (0.14 g, 0.50 mmol) in DMF (5 mL) was added 2,3-dihydro-1H-indene-2-carboxylic acid (0.08 g, 0.50 mmol), HOBt (0.06 g, 0.47 mmol), EDC (0.103 g, 0.54 mmol) followed by Hunig's base (0.14 mL, 0.83 mmol). The resulting mixture was stirred overnight at room temperature before addition of satd. aq. NaHCO$_3$ and EtOAc. The separated aq. layer was extracted again with ethyl acetate. The combined organic layers were washed with satd. aq. NaCl (3×) and dried (MgSO$_4$). Purification by flash chromatography (MeOH/CH$_2$Cl$_2$) gave an oil (0.024 g, 0.06 mmol, 11% yield). HPLC purity 96% ($t_R$=5.12 min). NMR (500 MHz, CDCl$_3$) δ 7.1-7.2 (m, 5H), 6.7-6.8 (m, 3H), 5.9 (d, 1H), 4.9 (s, 1H), 3.0-3.1 (m, 5H), 2.8 (d, 4H), 2.6-2.7 (m, 5H), 1.8 (m, 4H). ESI-MS m/z 423.1 (M+H$^+$).

Compound 3j

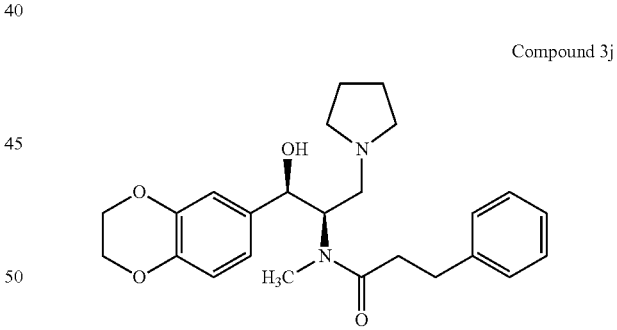

N-((1R,2R)-1-(2,3-dihydrobenzo[b][1,4]dioxin-6-yl)-1-hydroxy-3-(pyrrolidin-1-yl)propan-2-yl)-N-methyl-3-phenylpropanamide. To a 0° C. solution of compound 5 (0.2 g, 0.72 mmol) in THF (4 mL) was added Hunig's Base (0.09 g, 0.72 mmol) followed by hydrocinnamoyl chloride (0.12 g, 0.72 mmol) dropwise. The resulting mixture was allowed to stir overnight at room temperature, diluted with EtOAc and washed with satd. aq. NaHCO$_3$, satd. aq. NaCl and dried over MgSO$_4$. Purification by flash silica chromatography (MeOH/CH$_2$Cl$_2$) gave a yellow oil (0.12 g, 0.29 mmol, 41% yield). HPLC purity 98.4% ($t_R$=5.02 min). NMR (500 MHz, CDCl$_3$) δ 7.2 (s, 1H), 7.1-7.2 (m, 4H), 6.8-6.9 (m, 3H), 4.8 (s, 1H), 4.3 (s, 4H), 2.9 (s, 3H), 2.8-3.2 (m, 4H), 2.5-2.6 (m, 2H), 1.8-2.1 (m, 2H), 1.5-1.8 (m, 4H). ESI-MS m/z 425.1 (M+H$^+$).

Compound 6

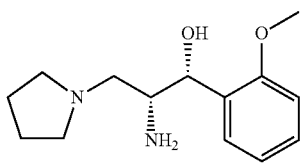

(1R,2R)-2-amino-1-(2-methoxyphenyl)-3-(pyrrolidin-1-yl)propan-1-ol. Prepared in a manner similar to (1R,2R)-2-amino-1-(2,3-dihydrobenzo[b][1,4]dioxin-6-yl)-3-(pyrrolidin-1-yl)propan-1-ol as described in U.S. Pat. No. 6,855,830 and starting with 2-methoxy-benzaldehyde. Clear oil. HPLC system A 98% ($t_R$=4.52 min) NMR (500 MHz, CDCl$_3$) δ 7.47-7.48 (d, 1H), 7.25-7.29 (1H, M), 6.80-7.02 (m, 1H), 6.87-6.88 (d, 1H), 5.065 (s, 1H), 3.83 (s, 3H), 3.71-3.73 (1H, M), 3.22-3.24 (m, 1H), 2.80-2.84 (m, 1H), 2.55-2.58 (m, 5H), 1.80 (m, 4H).

Compound 7

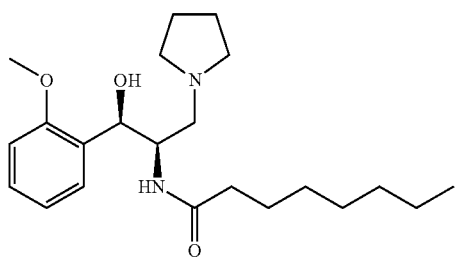

N-((1R,2R)-1-hydroxy-1-(2-methoxyphenyl)-3-(pyrrolidin-1-yl)propan-2-yl)octanamide. To a 0° C. solution of (1R,2R)-2-amino-1-(2-methoxyphenyl)-3-(pyrrolidin-1-yl)propan-1-ol (0.1 g, 0.40 mmol) (compound 6) in THF (5 ml) was added Hunig's Base (0.07 g, 0.52 mmol), followed by the dropwise addition of octanoyl chloride (0.07 g, 0.40 mmol). The resulting mixture was allowed to stir overnight at room temperature, diluted with EtOAc, and washed with satd. aq. NaHCO$_3$, satd. aq. NaCl, and dried over MgSO$_4$. Purified by flash silica chromatography (MeOH/CH$_2$Cl$_2$) to give a yellow oil (0.03 g, 0.09 mmol, 22% yield). HPLC purity 93% ($t_R$=5.3 min) NMR (500 MHz, CDCl$_3$) δ 7.4 (m, 1H), 7.2-7.3 (m, 1H), 6.9-7.0 (m, 1H), 6.8-6.9 (m, 1H), 6.0-6.1 (m, 1H), 5.3 (d, 1H), 4.2-4.3 (m, 1H), 3.8 (s, 3H), 2.9-3.0 (m, 3H), 2.5-2.7 (m, 4H), 2.0-2.1 (m, 2H), 1.7-1.8 (m, 4H), 1.9-2.0 (m, 2H), 1.2-1.4 (m, 6H), 0.8-0.9 (t, 3H). ESI-MS m/z 377.2 (M+H $^+$).

Compound 8

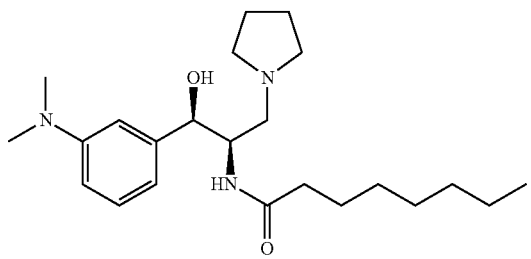

N-((1R,2R)-1-(3-(dimethylamino)phenyl)-1-hydroxy-3-(pyrrolidin-1-yl)propan-2-yl)octanamide. Prepared in a manner similar to that described for Compounds 6 and 7 starting with 3-(N,N-dimethylamino)benzaldehyde. NMR (500 MHz, CDCl$_3$) δ 7.2-7.3 (m, 2H), 6.6-6.8 (m, 2H), 5.9 (br d, 1H), 5.0 (d, 1H), 4.2-4.3 (m, 1H), 3.9 (s, 1H), 2.9-3.0 (s, 6H), 2.5-2.7 (m, 6H), 2.0-2.1 (m, 2H), 1.7-1.8 (m, 4H), 1.9-2.0 (m, 2H), 1.2-1.4 (m, 7H), 0.8-0.9 (t, 3H). ESI-MS m/z 390.3 (M+H$^+$).

Compound 9

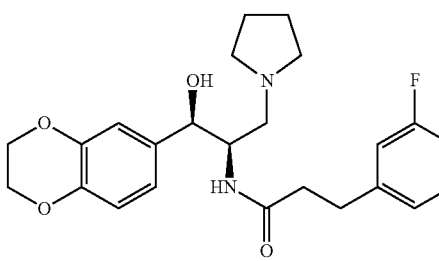

N-((1R,2R)-1-(2,3-dihydrobenzo[b][1,4]dioxin-6-yl)-1-hydroxy-3-(pyrrolidin-1-yl)propan-2-yl)-3-(3-fluorophenyl)propanamide. NMR (500 MHz, DMSO-d6) δ 7.1-7.3 (m, 2H), 6.6-6.9 (m, 5H), 6.1 (s, 1H), 4.9 (s, 1H), 4.2 (s, 4H), 2.8-3.2 (m, 4H), 2.5-2.6 (m, 4H), 1.8-2.1 (m, 2H), 1.5-1.8 (m, 4H). ESI-MS m/z 429.2 (M+H $^+$).

Compound 10

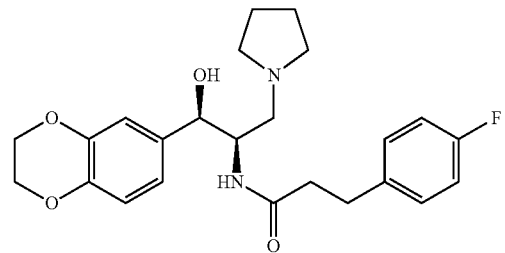

N-((1R,2R)-1-(2,3-dihydrobenzo[b][1,4]dioxin-6-yl)-1-hydroxy-3-(pyrrolidin-1-yl)propan-2-yl)-3-(4-fluorophenyl)propanamide. NMR (500 MHz, DMSO-d6) δ 7.1-7.2 (m, 2H), 6.8-6.9 (m, 2H), 6.7-6.8 (m, 2H), 6.6-6.7 (m, 1H), 5.8 (d, 1H), 4.9 (s, 1H), 4.3 (m, 4H), 4.2 (br s, 1H), 2.8-2.9 (m, 2H), 2.7-2.9 (m, 2H), 2.5-2.6 (m, 4H), 2.3-2.4 (m, 2H), 1.6-1.7 (br s, 4H). ESI-MS m/z 429.0 (M+H $^+$).

Compound 11

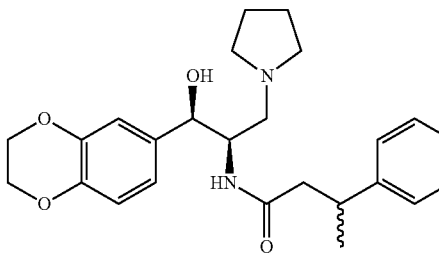

N-((1R,2R)-1-(2,3-dihydrobenzo[b][1,4]dioxin-6-yl)-1-hydroxy-3-(pyrrolidin-1-yl)propan-2-yl)-3-phenylbutanamide (mixture of diastereomers). NMR (500 MHz, DMSO-d6) δ 7.2-7.4 (m, 5H), 6.6-6.8 (m, 3H), 6.4 (d, 1H), 5.8-5.8 (m, 2H), 4.9 (m, 1H), 4.7 (m, 1H), 4.2 (m, 4H), 4.1 (br s, 1H), 2.8-2.9 (m, 1H), 2.3-2.7 (m, 3H), 2.5-2.6 (m, 3H), 1.5-1.6 (m, 4H), 1.6-1.9 (m, 3H). ESI-MS m/z 425.1 (M+H $^+$).

Compound 12

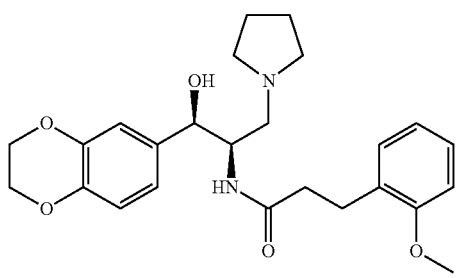

N-((1R,2R)-1-(2,3-dihydrobenzo[b][1,4]dioxin-6-yl)-1-hydroxy-3-(pyrrolidin-1-yl)propan-2-yl)-3-(2-methoxyphenyl)propanamide. NMR (500 MHz, DMSO-d6) δ 7.0-7.2 (m, 3H), 6.6-6.9 (m, 5H), 6.0 (br s, 1H), 5.9 (br s, 1H), 3.8-3.9 (m, 1H), 4.3 (s, 3H), 3.7 (s, 4H), 2.8-2.9 (m, 3H), 2.3-2.8 (m, 4H), 1.7-1.8 (m, 4H), 1.7-(m, 3H). ESI-MS m/z 441.1 (M+H $^+$).

Compound 13

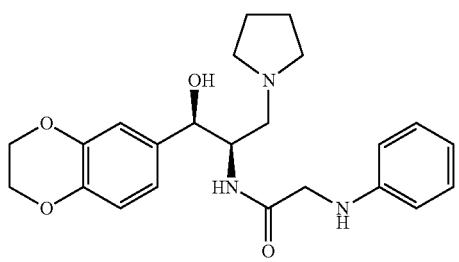

N-((1R,2R)-1-(2,3-dihydrobenzo[b][1,4]dioxin-6-yl)-1-hydroxy-3-(pyrrolidin-1-yl)propan-2-yl)-2-(phenylamino)acetamide. NMR (500 MHz, DMSO-d6) δ 7.2-7.3 (m, 2H), 7.0-7.1 (m, 1H), 6.7-6.8 (m, 2H), 6.6 (d, 1H), 6.5-6.6 (m, 3H), 4.9 (s, 1H), 4.3 (s, 4H), 4.1 (br s, 1H), 3.6-3.7 (m, 2H), 2.7-2.8 (m, 2H), 2.5-2.6 (m, 4H), 1.7 (m, 4H), 1.5-1.6 (br, 2H). ESI-MS m/z 412.0 (M+H $^+$).

Compound 14

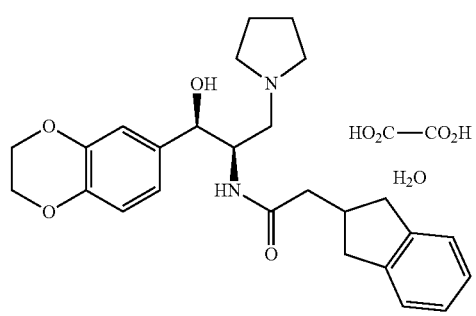

2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide oxalate monohydrate. NMR (500 MHz, DMSO-d6) δ 8.23-8.26 (1H, d), 7.59-7.64 (m, 4H), 7.37 (s, 1H), 7.30 (1H, s), 5.22 (d, 1H), 4.71-4.80 (m, 1H), 4.62-4.71 (m, 4H), 3.64-3.90 (m, 5H), 3.17-3.30 (m, 2H), 3.01 (s, 4H), 2.64-2.95 (m, 4H) 2.2-2.4 (m, 2H), 2.2 (s, 4H). ESI-MS m/z 437.2 (M+H $^+$) mp=149-150° C.

GCS Inhibition

GCS inhibitors are known. Some GCS inhibitors, e.g., eliglustat and miglustat, possess sufficient activity to inhibit GCS activity, and therefore have been proposed as suitable for treating diseases related to glycolipid accumulation. Unfortunately, these compounds and/or their pharmacological profile are not completely satisfactory. For example, miglustat is capable of crossing the BBB, but does not achieve levels in the CNS that exceed its IC$_{50}$ and many of its effects are either off target or due to its potential activity as a chemical chaperone for beta-glucocerebrosidase. Accordingly diseases which require a therapeutic drug to cross the BBB by cannot be treated. Consequently, there is an ongoing need to provide new compounds that effectively and selectively inhibit GCS, and, in some embodiments, are capable of crossing the BBB. Compounds of structural formula (I) exhibit these beneficial properties.

To demonstrate the ability of the present GCS inhibitors to reduce glycolipid accumulation in lysosomes and to cross the BBB, the above compounds of the invention were prepared and assayed.

In particular, compounds having activity against GCS and that lack MDR1 recognition were discovered using the D-threo-1-phenyl-2-decanoylamino-3-morpholino-propanol (PDMP) pharmacophore. Modifications of the carboxamide N-acyl group were made to lower total polar surface area and rotatable bond number. The compounds were screened for inhibition of GCS in broken cell and whole cell assays, and for MDR1 substrate recognition. Compounds of structural formula (I), e.g., 2-(2,3-dihydro-1H-inden-2-yl)-N-((1R, 2R)-1-(2,3-dihydrobenzo[b][1,4]dioxin-6-yl)-1-hydroxy-3-(pyrrolidin-1-yl)propan-2-yl)acetamide (compound 3h), were found to inhibit GCS at low nanomolar concentrations with little to no apparent recognition by MDR1. In addition, intraperitoneal administration of compound 3h to mice for 3 days resulted in a significant dose dependent decrease in brain glucosylceramide content, an effect not seen in mice dosed in parallel with eliglustat tartrate.

Modifications to the PDMP pharmacore resulted in new GCS inhibitors that retain activity against GCS and eliminate substrate specificity for the MDR1 protein. As a result, novel compounds that inhibit GCS in both the brain and peripheral organs have been provided.

Assays
Materials

N-((1R,2R)-1-(2,3-dihydrobenzo-[b][1,4]dioxin-6-yl)-1-hydroxy-3-(pyrrolidin-1-yl)propan-2-yl)octanamide (eliglustat tartrate, compound 3a) was provided by Genzyme Corporation. [$^3$H]Vinblastine and [$^{14}$C]mannitol were purchased from American Radiolabeled Chemicals (St Louis, Mo.).

In the tests described below, compound 3h, as the free base, also is referred to as EtDO-P1P2 and ethylenedioxy-P1P2. Salts of compound 3h also are referred to as EtDO -P1P2 oxalate or ethylenedioxy-PlP2 tartrate, for example.

GCS Activity

Enzyme activity was measured as described previously (9). Madin-Darby canine kidney (MDCK) cell homogenates (120 µg of protein) were incubated with uridine diphosphate-[$^3$H] glucose (100,000 cpm) and liposomes consisting of 85 µg of octanoylsphingosine, 570 µg of dioleoylphosphatidylcholine, and 100 µg of sodium sulfatide in a 200 µL reaction mixture and kept for 1 h at 37° C. PDMP derivatives dissolved in dimethyl sulfoxide (final concentration <1% which did not affect enzyme activity) were dispersed into the reaction mixture after adding the liposomes.

GCS Inhibition in MDCKII Cells

Parental (WT-)MDCKII cells and MDCKII cells retrovirally transduced with human MDR-1 cDNA were obtained from the Netherlands Cancer Institute. Both cell lines were routinely maintained in medium consisting of Opti-MEM/F 12 (1:1), 5% FBS, 100 U/mL of penicillin, 100 µg/mL streptomycin and 200 mM L-glutamine. MDCKII cells were newly thawed from frozen ampules every two months. Protein levels of MDR1 in MDR1-MDCKII cells were measured monthly, and MDR1-MDCKII cell passages were immediately terminated when a reduction of MDR1 levels was observed by Western blot using anti-human MDR1 monoclonal antibody (Abcam C219).

Stock solutions of water-insoluble glycosphingolipid inhibitors (100 mM) were prepared by dissolving each inhibitor into 100% ethanol as previously described (3). The inhibitor-ethanol solutions then were diluted 50× into 2 mM delipidated bovine serum albumin-phosphate buffered saline solution to make water-soluble glycosphingolipid inhibitor-bovine serum albumin complexes. The inhibitor-bovine serum album complexes were sterile-filtered and stored at −20° C. Prior to use, portions of the inhibitor-bovine serum albumin complexes were further diluted with Opti-F12 to make treatment solutions. Equal amounts of bovine serum albumin and ethanol were added into the control cultures. WT and MDR1-MDCKII cells ($5 \times 10^5$) were seeded into 10-cm culture dishes containing 10 ml of Opti-F12 with 5% FBS. After 24 hours, the medium was replaced with fresh serum-free Opti-F12 medium, and cells were exposed to candidate GCS inhibitors at concentrations of 0, 1, 3, 10, 30, 100 and 300 nM for 24 hours.

Cell Lipid Analysis

Following inhibitor treatment, whole cellular lipids of wild type and MDR1-MDCKII cells were extracted as previously described in detail (10). Briefly, cells were washed with ice-cold phosphate buffered saline, fixed by methanol, and collected with rubber scraper. Chloroform was then added to yield a theoretical ratio of chloroform:methanol:water at 1:2:0.8 (v/v/v) to form a mono-phase. Cell debris and proteins were removed by centrifugation at 2200×g for 30 min. The supernatants were portioned by adding chloroform and 0.9% NaCl. The lower organic phases containing neutral glycosphingolipids lipids were washed with methanol and 0.9% NaCl, and subjected to base- and acid-hydrolysis (10). A portion of purified glycosphingolipids normalized to 100 nmol of total phospholipids was analyzed by high performance thin layer chromatography. The thin layer chromatography separations were processed twice. The plate pretreated with 1% sodium borate was first developed in a solvent system consisting of chloroform/methanol (98/2, v/v). After air drying, the plate was then developed in a solvent system containing chloroform/methanol/water (70/30/4, v/v/v). The levels of glucosylceramide were detected by charring with 8% cupric sulfate in 8% phosphoric acid, and quantified by densitometric scanning using ImageJ, NIH Image. Image data was analyzed, and the $IC_{50}$ of each inhibitor was calculated using GraphPad Prism (version 5.03).

Vinblastine Transport

MDR1- and WT-MDCKII cells were grown to confluence on Transwell filters (12 well plates) in DMEM+10% FBS. The media was then replaced with fresh Dulbecco's modified Eagle medium and [$^3$H]vinblastine (0.5 µCi/ml; 10 µM final unlabeled vinblastine concentration) and [$^{14}$C]mannitol (0.25 µCi/mL; an extracellular space marker) was added to the apical chamber. Uptake was measured over 2 hours at 37° C. At that time, uptake was stopped by washing each side of the membrane 3× with ice-cold PBS. Vinblastine uptake into the cells, after correction for any remaining adherent extracellular contamination, was calculated as described previously (11). To investigate the effect of experimental drugs on MDR-mediated transport, those compounds were added to the apical chamber (1-100 µM) during vinblastine uptake and the uptake results expressed as a % of that with vehicle alone.

In Vivo Studies

C57BL/6 mice were maintained on regular chow in specific-pathogen-free facilities. All animal studies were performed under the review of the University of Michigan Committee on the Use and Care of Animals and conformed to the National Institutes of Health Guide for the Care and Use of Laboratory Animals. Injection solutions were prepared from inhibitor-ethanol stock solution (100 mM) A portion of the stock solution was evaporated under a stream of $N_2$ gas. Dried eliglustat tartrate (compound 3a) was directly dissolved into 1× phosphate buffered saline. Compound 3h was dissolved with 250 µL of water plus 13.7 µL of 0.5 N HCl by hand shaking and gentle vortexing resulting in a 1 or 3 mg/ml of solution. The acidic solution was neutralized by mixing 100 µL of 10× phosphate buffered saline with 636.3 µL of water to bring the total volume to one ml. Inhibitor solutions were sterilized by passage through a 0.2 µM filter. Inhibitor recovery after filtration was confirmed by UV spectrometry and exceeded 99%. For control injections, phosphate buffered saline containing the same amount of HCl was used. Inhibitors were given to 6 to 8 week old female or male C57BL/6 mice by intraperitoneal injection volume at 1% of body weight.

Mouse Tissue Lipid Analysis

Lipid extractions of liver, kidney, and brain were performed as previously described (7). Briefly, frozen liver (about 0.5 g), two kidneys (about 0.3 g) and whole brain (about 0.4 g) were individually homogenized in sucrose buffer (250 mM sucrose, pH 7.4, 10 mM HEPES and 1 mM EDTA), at 0.2 g tissue/1 mL of sucrose buffer, with a Tri-R homogenizer. Each 0.8 mL of homogenate was mixed with 2 mL of methanol and 1 mL of chloroform, bath sonicated for 1 min and incubated at room temperature for 1 h. Tissue debris were removed by centrifugation at 2,400×gravity for 30 min. The pellets were re-extracted by mixing with 1 mL of methanol, 0.5 mL of chloroform and 0.4 mL of 0.9% NaCl (chloroform/methanol/0.9% NaCl, 1:2:0.8), incubated at room temperature for 1 h and centrifuged at 2,400×gravity for another 30 min. Two extracts were combined and mixed with 4.5 mL of chloroform and 1.2 mL of 0.9% NaCl (chloroform/methanol/0.9% NaCl, 2:1:0.8). After centrifugation at 800× gravity for 5 min, lower layer was washed with 3 mL of methanol and 2.4 mL of 0.9% NaCl. Second washing was carried with 3 mL of methanol, 2 mL of water and 0.4 mL of 0.9% NaCl followed by a 5 min centrifugation at 800×gravity. The resultant lower phase was collected and dried under a stream of $N_2$ gas.

The analysis of neutral glycosphingolipids from mouse liver, kidney, and brain was processed after alkaline methanolysis. Kidney lipids were incubated with 2 mL of chloroform and 1 ml of 0.21N NaOH in methanol for 2 h (kidney) or 7.5 h (liver and brain) at RT. The lipid extract was normalized to 0.5 µmol of total phospholipid phosphate (liver and kidney) or 2 µmol of total phospholipid phosphate (brain) for high performance thin layer chromatography analysis. After alkaline methanolysis, the brain lipids were passed through a silica gel column (7). Borate-impregnated thin layer chromatography plates were developed in a two solvent system.

Plates were first developed in chloroform/methanol (98:2, v/v). The plates loaded with kidney and liver lipids were then developed in chloroform/methanol/water (64:24:4, v/v/v), and brain lipids were further separated in chloroform/methanol/water (60:30:6, v/v/v). GlcCer levels were quantified by comparison to known standards.

Assay Results

The GlcCer content of WT- and MDR1-MDCKII cells was measured as a function of inhibitor concentration by the above-described assays to confirm that eliglustat tartrate (compound 3a) is a substrate for the MDR1 transporter. FIG. 1 shows the concentration dependent change in GlcCer content of WT-MDCKII and MDR-MDCKII cells in response to eliglustat tartrate. MDCK cells were cultured in the presence of eliglustat tartrate as described in the Methods section. After exposure to the inhibitor for 24 h, the cells were harvested and the lipids extracted and analyzed also as described in the Methods section. The data represent the mean±S.D. (n=3).

A significant rightward shift in the concentration response curve was observed for the reduction in GlcCer levels in the MDR1 expressing cells. The $IC_{50}$ values for the WT and MDR1 expressing cells were 13.7 and 31.7 nm, respectively. The interaction of eliglustat with MDR1 was further examined by measuring [$^3$H]vinblastine (an MDR substrate) transport in MDR1-MDCKII cells. Eliglustat produced a dose-dependent increase in [$^3$H]vinblastine uptake similar to that found for verapamil, a known MDR1 inhibitor (FIG. 2).

Figure 2:
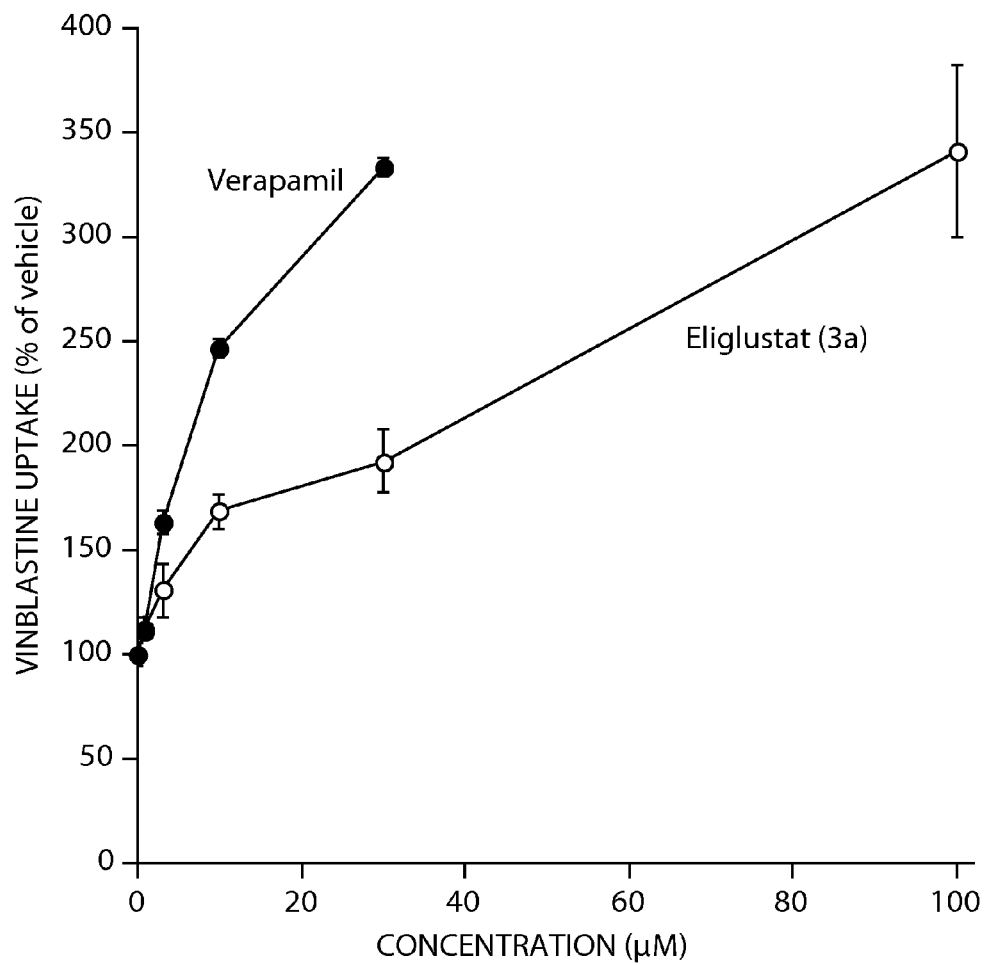
FIG. 2 is a graph of vinblastine uptake (% of vehicle) vs. verapamil and eliglustat concentration (μM)

FIG. 2 shows the effects of different concentrations of compound 3a (eliglustat) and verapamil (a known MDR1 inhibitor) on the uptake of [$^3$H]vinblastine into MDR1-MDCKII cells. Values are expressed as a % of vehicle-treated cells and are given as means±S.E (n=3). With vehicle treatment, [$^3$H]vinblastine uptake into MDR1-MDCKII cells was 13.6±1.7% of that in WT-MDCKII cells.

The compounds of structural formula (I) attenuated significant differences between key physical chemical properties of compound 3a (eliglustat) and successful central nervous system (CNS) drugs. Differences between the physical chemical properties of CNS versus non-CNS drugs are known (17-19), and vary significantly between the two groups. Compounds possessing molecular parameters outside of the ranges for CNS drugs tend to either have poor passive diffusion through cell membranes or be substrates for MDR1 mediated efflux. The range of tolerated physical chemical properties observed for CNS-active agents is significantly narrower than the whole of oral therapeutics because of the unique physical characteristics of the BBB (20,21). Specifically, the endothelial cells of the cerebral capillaries have extraordinarily tight junctions, requiring compounds to pass through entirely via the transcellular route by passive diffusion. Furthermore, the xenobiotic efflux transporter MDR1 in the BBB efficiently expels a wide variety of substrates.

A comparison of the computed property values for compound 3a relative to the mean values for the approved CNS drugs shows significant divergences (>1 SD) in molecular weight (MW), topological polar surface area (TPSA), number of hydrogen bond acceptors (HBA), number of hydrogen bond donors (HBD), and rotatable bonds (RotB). A reduction in TPSA is predictive of improved BBB permeability.

The activity of the GCS inhibitors at inhibiting GlcCer production in the broken cell assay is summarized in Table 1. Benzyl carbamate compound 3b retained the enzyme inhibitory activity of compound 3a, confirming a similar observation in a related template (13). The 3-propionamide compound 3c, lower in TPSA than compound 3b, was equally potent. Adjusting the length of the tether to the phenyl group revealed that a 3-carbon tether (compound 3e) was optimal ($IC_{50}$=80 nM).

Conformational restriction of the tether to further reduce number of rotatable bonds provided inventive compounds 3f-3i. Among these, 2-indanylmethyl (compound 3h) displayed a striking improvement in activity ($IC_{50}$=27 nM) and, represents the most potent GCS inhibitor reported to date.

TABLE 1

| | | | | | | | Broken Cell[a] | WT-MDCK[b] | MDR-MDCK[c] | |
| Cmpd | $R^1$ | $R^2$ | MW | TPSA (Å$^2$) | SLogP | RotB | $IC_{50}$ (nM) | $IC_{50}$ (nM) | $IC_{50}$ (nM) | MDR/WT[d] |
|---|---|---|---|---|---|---|---|---|---|---|
| 3a | H | —$C_7H_{15}$ | 404.5 | 71.0 | 3.53 | 12 | 149 | 13.7 | 31.7 | 2.3 |
| 3b | H | —$OCH_2Ph$ | 412.5 | 80.3 | 3.24 | 9 | 144 | 7.3 | 47.1 | 6.5 |
| 3c | H | —$CH_2CH_2Ph$ | 410.5 | 71.0 | 2.80 | 9 | 134 | 23.5 | 86.7 | 3.7 |
| 3d | H | —$CH_2Ph$ | 396.5 | 71.0 | 2.41 | 8 | >2000 | ND | ND | ND |
| 3e | H | —$CH_2CH_2CH_2Ph$ | 424.5 | 71.0 | 3.19 | 10 | 80 | 254 | 1440 | 5.7 |
| 3f | H | - E-CH=CHPh | 408.5 | 71.0 | 2.88 | 8 | 379 | 80.7 | 389 | 4.8 |
| 3g | H | -trans-2-Ph-cyclopropyl | 422.5 | 71.0 | 2.97 | 8 | 90 | 27.3 | 78.1 | 2.9 |
| 3h | H | —$CH_2$-indan-2-yl | 436.5 | 71.0 | 2.97 | 8 | 27 | 15.3 | 24.3 | 1.6 |
| 3i | H | -indan-2-yl | 422.5 | 71.0 | 2.58 | 7 | 107 | 151 | 3210 | 21 |
| 3j | $CH_3$ | —$CH_2CH_2Ph$ | 424.5 | 62.2 | 3.14 | 9 | 158 | 59.4 | 1250 | 21 |

[a]Inhibition of GlcCer synthesis in broken wild-type MDCK cell preparations (mean of n>2experiments).
[b]Inhibition of GlcCer production in whole wild-type MDCKII cells.
[c]Inhibition of GlcCer production in MDCKII cells stably expressing human MDR1 (obtained from The Netherlands Cancer Institute).
[d]Ratio of MDR1-MDCKII $IC_{50}$ divided by WT- MDCKII $IC_{50}$.

$R^3$ for all compounds 3a-3j in Table 1 is

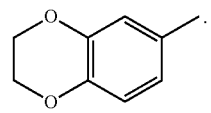

The ability of the tested compounds to inhibit GlcCer production in whole WT-MDCKII cells also is summarized in Table 1. Eliglustat (3a) was almost 10-fold more potent in whole cells than broken, possibly a result of intracellular accumulation. This phenomenon also was observed to varying degrees with other tested compounds. The ratio of broken cell $IC_{50}$ divided by whole cell $IC_{50}$ is weakly correlated negatively with MW ($R^2=0.58$) and positively with S log P ($R^2=0.50$), consistent with well-established medicinal chemistry principles that decreasing MW and increasing lipophilicity each improve passive permeability into cells (14).

The MDR-MDCKII cell line was used to help predict BBB permeability because it expresses an efflux transporter that is physiologically relevant to the brain endothelium (15, 16). It was assumed that $IC_{50}$ values for inhibition of GlcCer production in these cells correlates directly with intracellular drug levels, thereby providing a convenient and sensitive estimate of susceptibility to MDR-mediated efflux when compared with $IC_{50}$ values in WT-MDCKII cells. These results are included in Table 1. Significantly, the ratios of MDR-MDCKII $IC_{50}$ divided by WT-MDCKII $IC_{50}$ (MDR/WT) varied widely among the group, presumably reflecting a wide range of affinities for MDR1.

Figure 3:
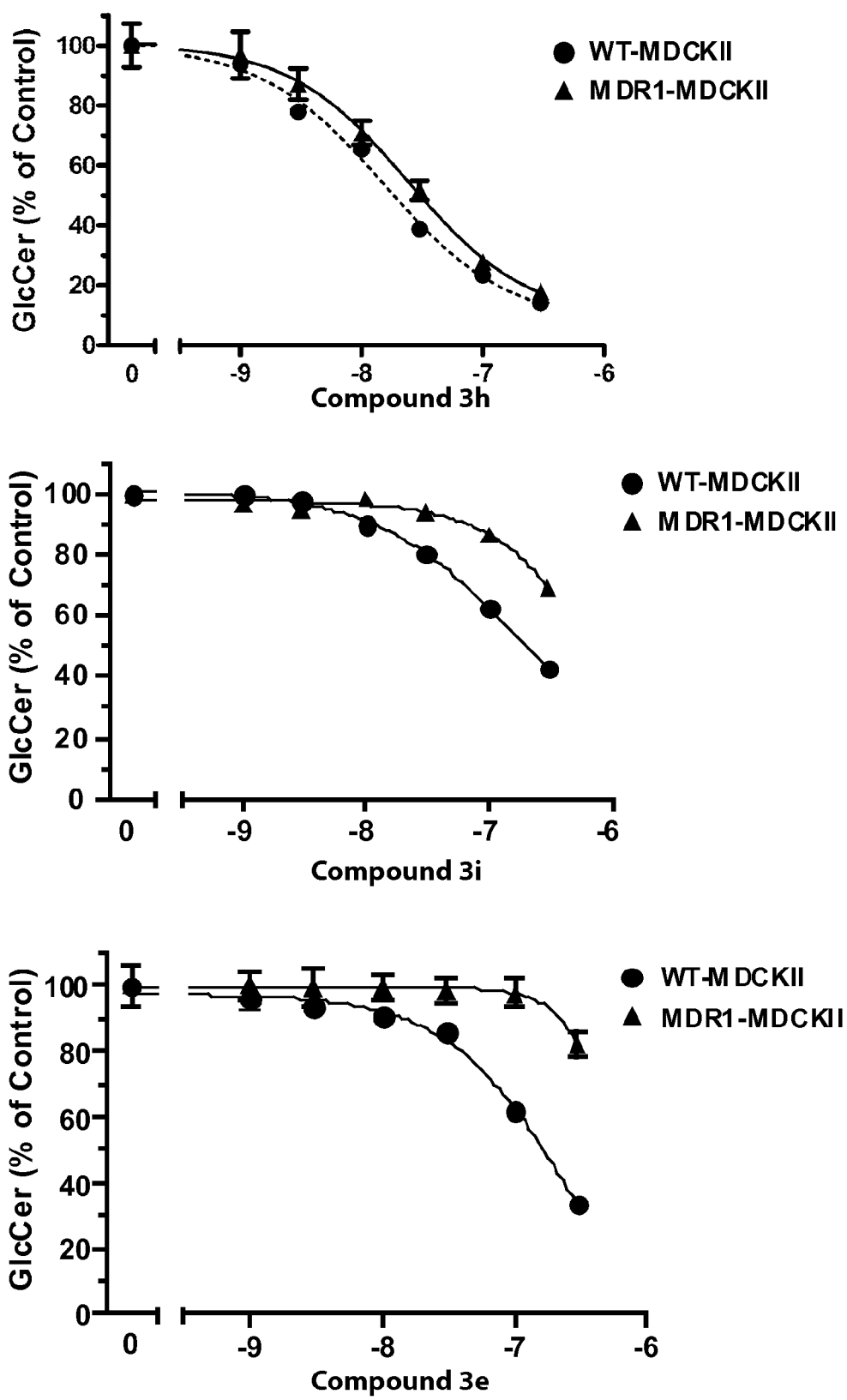
FIG. 3 contains graphs of GlcCer (% of control) in WT-MDCK11 and MDR1-MDCK11 cells vs. concentration of Compounds 3h and 3i.

Although several replacements for the C8 acyl group ($R^2$) of eliglustat were associated with the retention of nanomolar range inhibition of GlcCer in the WT cell line, compound 3h displayed a comparable $IC_{50}$ in the MDR1-MDCKII cells when compared to WT (<2-fold increase in $IC_{50}$). Deletion of a single endocyclic or exocyclic methylene group from the indane (compound 3i) was associated with a loss of activity in the MDR1-MDCKII line. A comparison of the dose-dependent changes in GlcCer levels for compounds 3e, 3h, and 3i is shown in FIG. 3.

Figure 4:
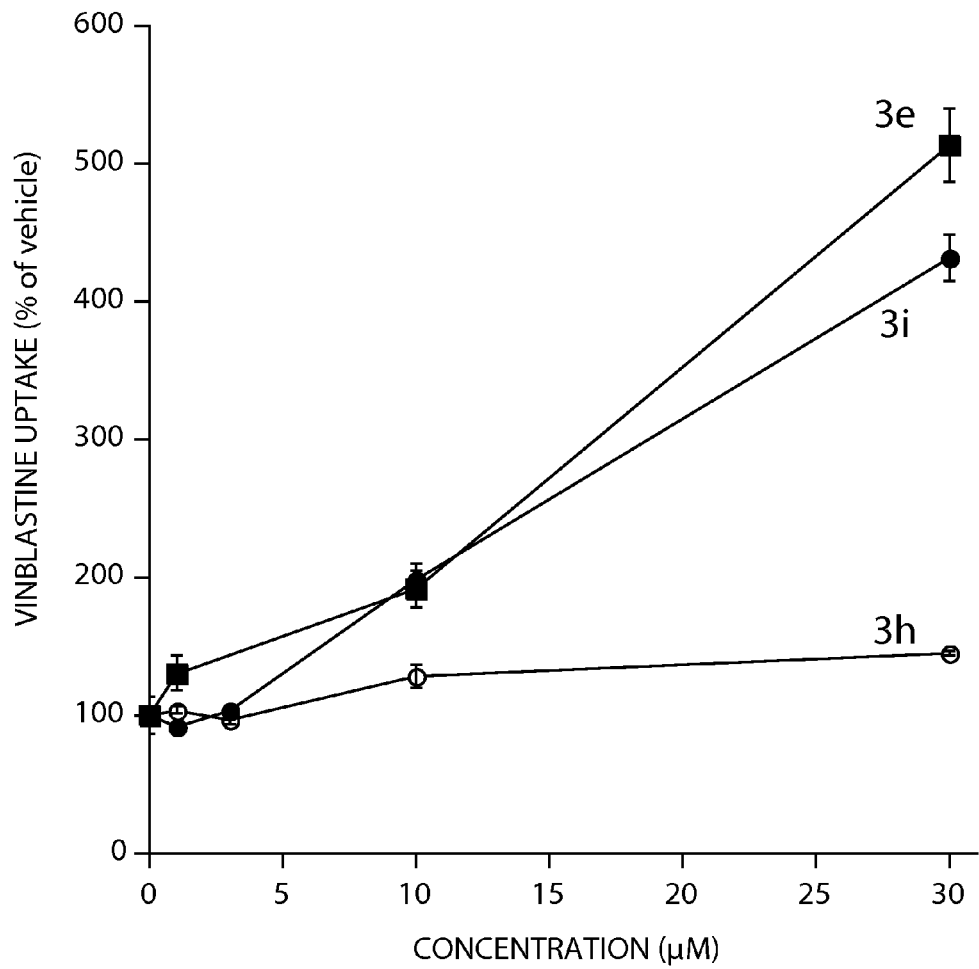
FIG. 4 is a graph of vinblastine uptake (% of vehicle) vs. concentration of compounds 3h, 3i, and 3e.

The potential interactions of the GCS inhibitor with MDR1 was further examined by determining their effects on [$^3$H] vinblastine transport in MDR1-MDCKII cells (FIG. 4). Consistent with the marked rightward shifts in the concentration response curve observed for compound 3i, a dose dependent increase in uptake in [$^3$H]vinblastine was also observed. In contrast, the compound 3h resulted in no significant dose dependent change in vinblastine uptake. These results are consistent with the absence of recognition of compound 3h as a substrate for MDR1.

FIG. 4 shows the effects of different concentrations of three GCS inhibitors on the uptake of [$^3$H]vinblastine into MDR1-MDCKII cells. Values are expressed as a % of vehicle-treated cells and are given as means±S.E (n=3). Compound 3h only differs from compound 3i by a single methylene spacer, and from compound 3e by a single bridging $CH_2$, but these changes result in changes in the interaction with MDR.

A range of GCS inhibitors was compared using both the GCS inhibition and vinblastine transport assays in WT- versus MDR1-MDCKII cells. There was reasonable agreement between the two assays with regard to changes in the presence of MDR1 (FIG. 5; r=0.50).

Figure 5:
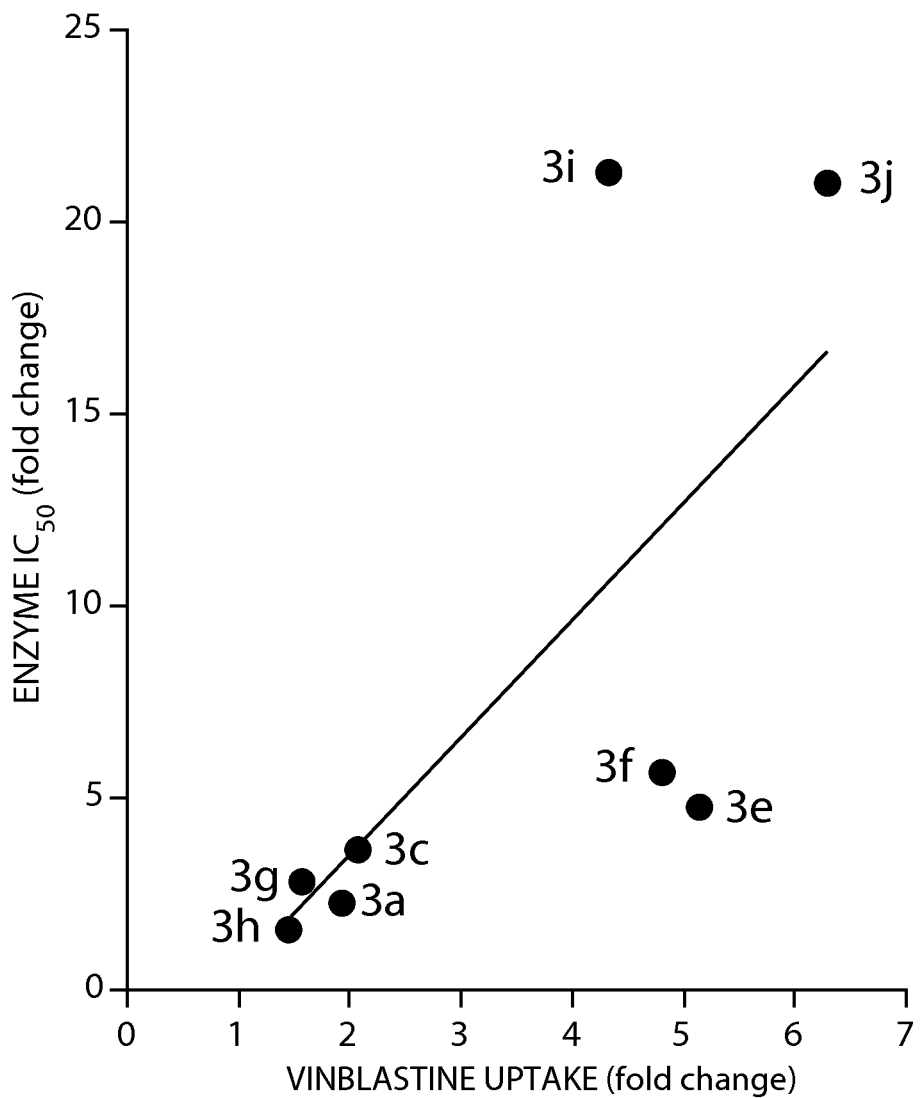
FIG. 5 is a graph of Enzyme $IC_{50}$ (fold change) vs. vinblastine uptake (fold change) for eight GCS inhibitors.

FIG. 5 shows the effects of different GCS inhibitors on two parameters, [$^3$H]vinblastine uptake into MDR1-MDCKII cells expressed as a fold change between 30 μM of the inhibitor and vehicle (x-axis) and the fold change in GCS $IC_{50}$ between MDR1- and WT-MDCKII cells (y-axis). For most compounds, a good correlation exists between the two parameters (the line represents equal changes). There was a significant correlation between both parameters although compounds 3i and 3j, showed noticeably greater effects on the enzyme $IC_{50}$ than compounds 3f and 3e despite similar magnitude effects on [$^3$H]vinblastine uptake. As assessed by both assays, compound 3h had the least interaction with MDR.

Based on these results and the $IC_{50}$ against the cell lysate synthase activity, compound 3h was chosen for in vivo studies. Six-week old wild type mice were initially treated with 10 mg/kg/day of compound 3h, or vehicle for 3 days and sacrificed 12 hours after the last injection (FIG. 6).

Figure 6:
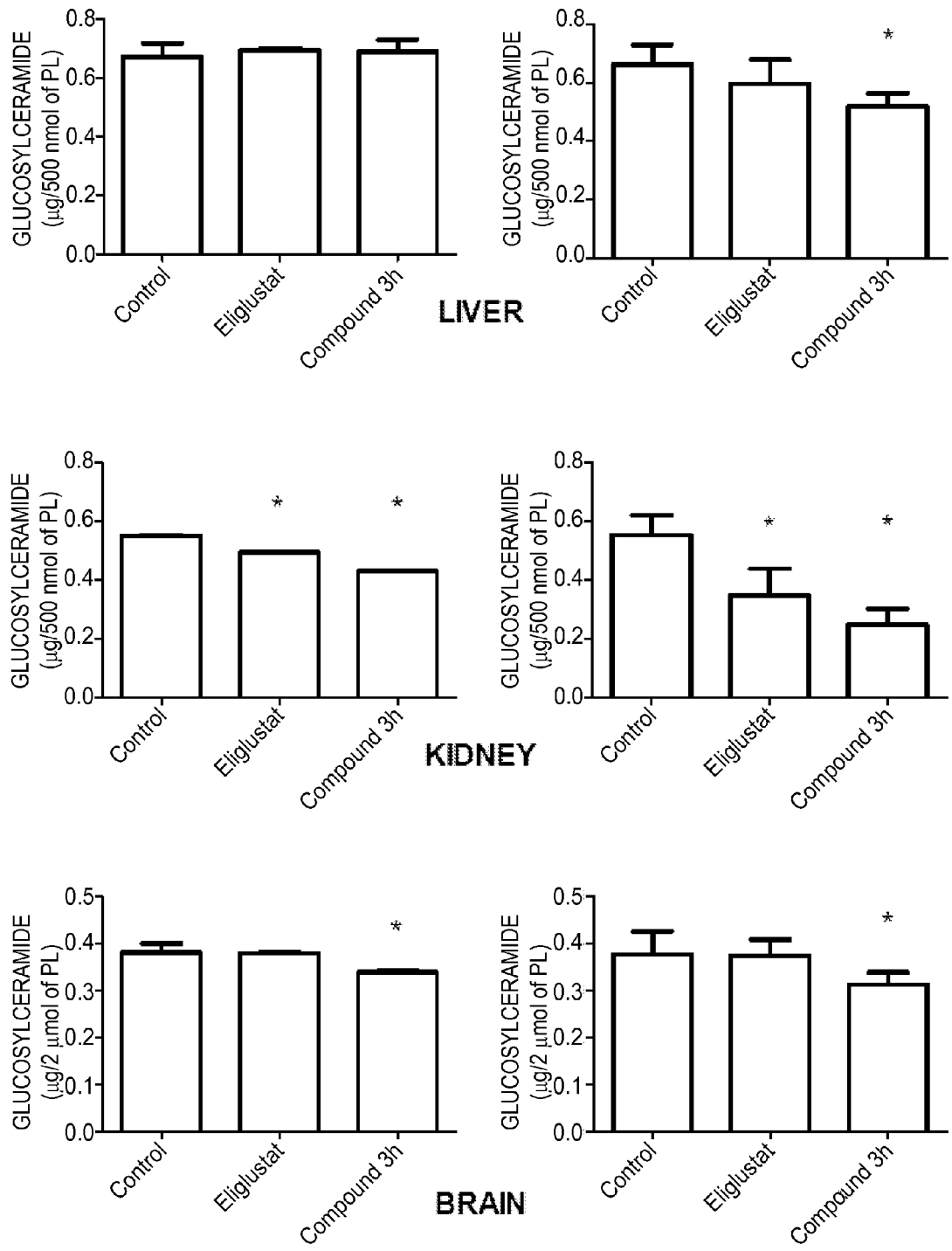
FIG. 6 contains bar graphs of glucosylceramide concentration vs. control, compound 3a, and compound 3h in the liver, kidney, and brain.

FIG. 6 shows the effect of eliglustat and compound 3h on organ GlcCer content after short term exposure. Six to eight weeks old C57BL/6 mice were treated with either vehicle or inhibitor for 3 days. Mice received 10 or 60 mg/kg/day i.p. of the respective inhibitor and were then euthanized 12 hours following the last injection. The data are expressed as mg of GlcCer normalized to 0.5 or 2 μmoles of phospholipid (PL) and represent the mean±S.D. and * denotes p<0.05 by student's T test versus vehicle treated control, n=4 except for 10 mg/kg/day treatment brain samples where n=3.

A ten percent decrease in the GlcCer levels in the brains of compound 3h inhibitor treated mice was observed without changes in the eliglustat or vehicle treated mice. When a higher dose of compound was employed (30 mg/kg q 12 h for 3 days), a more significant fall in brain GlcCer levels was observed (17%) in compound 3h treated mice without any changes in the vehicle treated or eliglustat treated mice. By contrast eliglustat lowered liver and kidney GlcCer levels, consistent with its previously reported effects. These data confirmed the ability of compound 3h to cross the BBB and inhibit GCS.

Importantly, in short term dosing, compound 3h significantly lowered brain GlcCer levels. In contrast, eliglustat (compound 3a) failed to demonstrate any change in brain cerebroside content under identical dosing conditions, even though compound 3a significantly lowered liver and kidney glycolipids. This finding confirmed that the lack of recognition of compound 3h by MDR was sufficient to result in a pharmacological response in the brain.

The therapeutic efficacy of compound 3h also was assessed in juvenile Sandhoff (Hexb−/−) mice. Sandhoff disease is an incurable neurodegenerative lysosomal storage disease (LSD) caused by autosomal recessive mutations in the beta subunit of β-hexosaminidase (34). The deficiency of Hexosaminidase A and B results in the storage of ganglioside GM2 and its asialo derivative (GA2) primarily in neurons. Hexb−/− mice suffer from neurodegeneration, neuroinflammation, demyelination, progressive motor deterioration, and premature death by 16 weeks (38, 37, 30, 31, 35).

Juvenile Hexb−/− mice treated with compound 3h showed significant reductions in total ganglioside and GM2 content in brain and liver. The ganglioside reductions in brain were similar to those reported previously in LSD mice treated with the imino sugars, NB-DNJ and NB-DGJ (32, 33, 23). The results summarized below show that compound 3h is an excellent candidate for substrate reduction therapy for prolonged treatment of peripheral and CNS LSDs.

Mice

The SV/129 Hexb−/− mice were obtained from the NIH. The mice were derived by the disruption of the murine Hexb gene and transferring this gene into the mouse genome via homologous recombination and embryonic stem cell technology as previously described (38). The genotypes of mice were determined by PCR as previously described. Mice were propagated and housed in plastic cages with filter tops containing Sani-Chip bedding (P.J. Murphy Forest Products Corp.; Montville, N.J.). Food and water were provided ad libitum. Nursing females were provided with cotton nesting pads for the duration of the experiment.

Compound 3h Treatment and Tissue Collection

Compound 3h oxalate salt, D-threo-3',4'-ethylenedioxy-1-phenyl-2-indanylacetoamino-3-pyrrolidino-1-propanol-oxalate, was suspended to a concentration of 1 mM in $CHCl_3$:$CH_3OH$ 1:2 (v/v). The solution was dried under nitrogen, resuspended in 3.6 ml distilled $H_2O$, then dissolved at 42° C.

in a shaking water bath. The solution was neutralized by adding 400 µl of 10× phosphate buffer saline (PBS), and was sterilized following passage through an Acrodisc 0.2 µm syringe filter (Sigma, St. Louis, Mo.). The final solution contained about 6.0 mg/ml of compound 3h. The mice were weighed daily and received intraperitoneal (i.p.) injections equivalent to 60 mg/kg from postnatal day 9 (p-9) to postnatal day 15 (p-15). Control mice received i.p. injections of PBS. Injections were performed using a Hamilton syringe (26 gauge, point style 2, 0.5 inch needle) (Hamilton, Reno, Nev.), and volumes ranged from 50 ul to 100 µl/mouse. The mice were sacrificed 4 hrs after the final injection on p-15. Cerebrum, cerebellum, and liver were dissected and frozen on dry ice to determine wet weight. The tissues then were homogenized in 3.0 ml distilled $H_2O$, and 150 µl of each homogenate was set aside for analysis of protein and lysosomal enzyme activities. The remaining homogenate was frozen at −80° C., lyophilized, then weighed before lipid extraction.

Enzyme Assays

β-hexosaminidase and β-galactosidase specific activities were measured using either 1 mM 4-methylumbelliferyl-N-acetyl-β-D-glucosaminide (Sigma-Aldrich, St. Louis, Mo.) or 4-methylumbelliferyl-β-D-galactopyranoside (Sigma-Aldrich, St. Louis, Mo.) as substrates, respectively (27). Tissue homogenates were centrifuged for 5 minutes at 2,000×g. The collected supernatants were dispensed in duplicate to BD Falcon 96-well plates on ice. Increasing volumes of 40 µM 4-methylumbelliferone (Sigma-Aldrich, St. Louis, Mo.) in 0.9% NaCl were used as standards. Plates were incubated at 37° C. for 30 minutes after the addition of substrate. The reaction was stopped by the addition of 0.5 M sodium carbonate (pH 10.7). A SpectraMax M5 micro-plate reader (Molecular Devices, Sunnyvale, Calif.) with excitation and emission set at 355 nm and 460 nm was used to estimate fluorescent emission of 4-methylumbelliferone. Total protein concentrations for each tissue were determined by mixing an aliquot of each sample with Bio-Rad Protein Dye Reagent (Bio-Rad, Hercules, Calif.) diluted 1:4 (v/v) in water. Increasing concentrations of bovine serum albumin (BSA) (Sigma-Aldrich, St. Louis, Mo.) were used as standards. Plates were incubated at room temperature for 15 minutes, and read at 595 nm in the SpectraMax M5. Specific enzyme activity was expressed as nmol/mg protein/hr.

Lipid Isolation, Purification, and Quantitation

Total Lipid Extraction

Lipid extraction of lyophilized tissue was performed overnight in 5 ml $CHCl_3$:$CH_3OH$ 1:1 (v/v). Samples were spun down at 2500 rpm for 20 min, and the supernatant was collected. Pellets were washed in 2 ml $CHCl_3$:$CH_3OH$ 1:1 (v/v), spun down again, and the total 7 ml of supernatant was brought up to a final volume of 19.6 ml at a ratio of 30:60:8 $CHCl_3$:$CH_3OH$:$dH_2O$ (v/v/v).

Ion Exchange Chromatography

Neutral lipids and cholesterol were separated from acidic lipids and gangliosides by ion exchange chromatography as we described (32, 28, 24). The total lipid extract, suspended in $CHCl_3$:$CH_3OH$:$dH_2O$, 30:60:8 by volume (solvent A), was applied to a DEAE Sephadex column (1.2 mL bed volume) that had been equilibrated prior with solvent A (28). The column was washed twice with 20 mL solvent A and the entire neutral lipid fraction, consisting of the initial eluent plus washes, was collected. This fraction contained cholesterol, phosphatidylcholine, phosphatidylethanolamine and plasmalogens, sphingomyelin, and neutral GSLs to include cerebrosides and asialo-GM2 (GA2). Next, acidic lipids were eluted from the column with 35 mL $CHCl_3$:$CH_3OH$:0.8 M Na acetate, 30:60:8 by volume. Gangliosides were separated from acidic phospholipids by Folch partitioning, base treated, and desalted as previously described (32, 28). Neutral lipids were dried by rotary evaporation and resuspended in 10 mL $CHCl_3$:$CH_3OH$ (2:1; v/v). A 4 mL aliquot was evaporated under nitrogen, base treated with 1 N NaOH, and Folch partitioned. The Folch lower phase containing GA2 was evaporated under nitrogen and resuspended in 4 mL $CHCl_3$:$CH_3OH$ (2:1; v/v).

Ganglioside Sialic Acid Quantification

Total ganglioside content was quantified before and after desalting using the resorcinol assay as previously described (28). Sialic acid values were fit to a standard curve using n-acetylneuraminic acid as a standard.

High Performance Thin Layer Chromatography

All lipids were analyzed qualitatively by high-performance thin-layer chromatography (HPTLC) according to previously described methods (28, 24, 25). Lipids were spotted on 10 cm×20 cm Silica gel 60 HPTLC plates (E. Merck, Darmstadt, Germany) using a Camag Linomat III auto-TLC spotter (Camag Scientific, Inc., Wilmington, N.C.). The amount of lipid per lane was equivalent to 1.5 µg of total sialic acid for gangliosides, and 70 µg, 200 µg, and 300 µg of tissue dry weight for neutral lipids, acidic lipids, and GA2, respectively. HPTLC plates were developed by a single 90 min ascending run with $CHCl_3$:$CH_3OH$:$dH_2O$ (55:45:10; v/v/v for gangliosides; 65:35:8, v/v/v for GA2) containing 0.02% $CaCl_2$-$2H_2O$. The plates were sprayed with either the resorcinol-HCl reagent or the orcinol-$H_2SO_4$ reagent and heated at 95° C. for 10 min to visualize gangliosides or GA2, respectively. For neutral and acidic lipids, plates were developed to a height of 4.5 cm (for neutral lipids) or 6.0 cm (for acidic lipids) with chloroform:methanol: acetic acid:formic acid: water 35:15:6:2:1 (v/v/v/v/v), then run to the top with hexane: diisopropyl ether: acetic acid 65:35:2 (v/v/v). The bands were visualized by charring with 3% cupric acetate in 8% phosphoric acid solution (36).

Quantitation of Individual Lipids

The percent distribution and density of the individual lipid bands was determined by scanning the HPTLC plates on a CAMAG Scanner III (Camag Scientific, Inc., Wilmington, N.C.). The total brain ganglioside distribution was normalized to 100%, and the percentage distribution values were used to calculate sialic acid concentration (micrograms of sialic acid per 100 mg dry weight) of individual gangliosides. The density values for neutral lipids, acidic lipids, and GA2 were fit to a standard curve and used to calculate individual concentrations expressed as milligrams per 100 mg dry weight. Oleyl alcohol was also run on the HPTLC plates as an internal standard for quantitation of cholesterol, and the neutral and acid phospholipids (36).

Results

Brain water content, β-hexosaminidase specific activity, and β-galactosidase specific activity were similar in the control and Hexb −/− mice treated with compound 3h at 60 mg/kg/day from p-9 to p-15 (Table 2). Water content is a sensitive indicator of brain development (39, 40). Body weight was slightly higher in the compound 3h-treated Hexb −/− mice than in the control Hexb −/− mice, and was similar to that seen in the normal Hexb +/− mice. Total sialic content in compound 3h-treated mice was significantly lower in the compound 3h-treated Hexb −/− mice than in the control Hexb −/− mice in cerebrum (11%) and cerebellum (14%), and liver (38%) (Table 3).

TABLE 2

Body weight, brain weight water content, and enzymatic activity in p-15 Sandhoff mice treated with compound 3h[a]

| Hexb genotype | Treatment | n[b] | Body Weight g | Wet Weight | | Water Content | |
|---|---|---|---|---|---|---|---|
| | | | | Cerebrum | Cerebellum | Cerebrum | Cerebellum |
| | | | | mg | | % | |
| +/− | PBS[c] | 4 | 8.7 ± 0.2 | 287.6 ± 2.5 | 94.1 ± 6.6 | 84.45 ± 0.01 | 83.72 ± 0.01 |
| −/− | PBS[c] | 4 | 7.8 ± 0.1 | 264.4 ± 6.8 | 102.0 ± 4.0 | 84.59 ± 0.01 | 84.09 ± 0.01 |
| −/− | 3h[d] | 3 | 9.0 ± 0.5 | 271.0 ± 2.3 | 87.7 ± 7.7 | 84.45 ± 0.01 | 83.88 ± 0.01 |

| Hexb genotype | Treatment | n[b] | Body Weight g | β-hexosaminidase specific activity | | β-galactosidase specific activity | |
|---|---|---|---|---|---|---|---|
| | | | | Cerebrum | Cerebellum | Cerebrum | Cerebellum |
| | | | | nmol/mg | | protein/hr | |
| +/− | PBS[c] | 4 | 8.7 ± 0.2 | 293.8 ± 3.5 | 107.5 ± 4.4 | 42.0 ± 1.6 | 33.2 ± 1.7 |
| −/− | PBS[c] | 4 | 7.8 ± 0.1 | 3.9 ± 0.1 | 3.0 ± 0.2 | 62.5 ± 3.4 | 61.1 ± 1.7 |
| −/− | 3h[d] | 3 | 9.0 ± 0.5 | 4.5 ± 0.0 | 2.8 ± 0.2 | 69.4 ± 6.0 | 54.8 ± 7.6 |

[a]Values are expressed as the mean ± standard error of the mean (SEM).
[b]n, the number of independent samples per group.
[c]Mice were injected daily from p-9 to p-15 with 1x Phosphate Buffer Saline.
[d]Mice were injected daily from p-9 to p-15 with 3h (EtDO-PIP2 oxalate) at 60 mg/kg/day.

TABLE 3

Effect of compound 3h on cerebrum, cerebellum, and liver ganglioside distribution in p-15 Sandhoff mouse.

| | Hex b Genotype | Treatment | n[c] | Total Siatic Acid | GM2 | | GM1 | |
|---|---|---|---|---|---|---|---|---|
| | | | | | Percent | Concentration | Percent | Concentration |
| Cerebrum | +/− | PBS[d] | 4 | 487 ± 11 | ND | ND | 7.9 ± 0.1 | 38.6 ± 1.3 |
| | −/− | PBS[d] | 4 | 500 ± 4 | 5.1 ± 0.3 | 25.6 ± 1.4 | 7.0 ± 0.4 | 34.8 ± 1.5 |
| | −/− | 3h[e] | 3 | 432 ± 11* | 2.8 ± 0.1** | 87.7 ± 7.7 | 6.1 ± 0.2 | 26.4 ± 1.6* |
| Cerebellum | +/− | PBS[d] | 4 | 373 ± 6 | ND | ND | 6.5 ± 0.3 | 24.2 ± 1.4 |
| | −/− | PBS[d] | 4 | 391 ± 17 | 5.3 ± 0.2 | 20.8 ± 1.6 | 5.8 ± 0.2 | 22.9 ± 1.9 |
| | −/− | 3h[e] | 3 | 318 ± 15* | 3.1 ± 0.1** | 9.8 ± 1.2** | 5.5 ± 0.4 | 17.4 ± 1.4 |
| Liver | +/− | PBS[d] | 4 | 57 ± 5 | 59.5 ± 1.4 | 33.6 ± 2.5 | 25.3 ± 0.7 | 14.5 ± 1.6 |
| | −/− | PBS[d] | 4 | 113 ± 6 | 68.7 ± 2.8 | 77.1 ± 4.6 | 18.0 ± 1.3 | 20.3 ± 1.9 |
| | −/− | 3h[e] | 3 | 70 ± 5** | 60.5 ± 1.3 | 42.1 ± 2.6** | 21.9 ± 1.5 | 15.4 ± 2.1 |

| | Hex b Genotype | Treatment | n[c] | GD3 | | G1a | |
|---|---|---|---|---|---|---|---|
| | | | | Percent | Concentration | Percent | Concentration |
| Cerebrum | +/− | PBS[d] | 4 | ND | ND | 44.5 ± 0.5 | 217.0 ± 5.6 |
| | −/− | PBS[d] | 4 | ND | ND | 43.0 ± 0.4 | 215.1 ± 3.1 |
| | −/− | 3h[e] | 3 | ND | ND | 43.4 ± 0.3 | 187.4 ± 5.2* |
| Cerebellum | +/− | PBS[d] | 4 | 5.3 ± 0.5 | ND | 22.8 ± 0.7 | 84.9 ± 3.6 |
| | −/− | PBS[d] | 4 | 4.9 ± 0.3 | 20.8 ± 1.6 | 22.7 ± 0.2 | 88.7 ± 4.5 |
| | −/− | 3h[e] | 3 | 4.3 ± 0.2 | 9.8 ± 1.2** | 24.1 ± 0.3* | 76.6 ± 3.7 |
| Liver | +/− | PBS[d] | 4 | ND | ND | 15.2 ± 1.2 | 8.6.5 ± 1.1 |
| | −/− | PBS[d] | 4 | ND | ND | 13.3 ± 1.6 | 15.1 ± 2.2 |
| | −/− | 3h[e] | 3 | ND | ND | 17.6 ± 1.1 | 12.2 ± 0.3 |

| | Hex b Genotype | Treatment | n[c] | GT1a/LD1 | | GD1b | |
|---|---|---|---|---|---|---|---|
| | | | | Percent | Concentration | Percent | Concentration |
| Cerebrum | +/− | PBS[d] | 4 | 4.0 ± 1.4 | 19.4 ± 1.4 | 9.6 ± 0.2 | 46.9 ± 1.3 |
| | −/− | PBS[d] | 4 | 3.8 ± 0.1 | 18.9 ± 0.2 | 8.4 ± 0.1 | 42.2 ± 0.9 |
| | −/− | 3h[e] | 3 | 4.8 ± 0.3 | 20.8 ± 0.7* | 7.3 ± 0.1** | 31.7 ± 0.5** |
| Cerebellum | +/− | PBS[d] | 4 | 5.6 ± 0.4 | 21.0 ± 1.7 | 22.8 ± 0.7 | 63.7 ± 2.3 |
| | −/− | PBS[d] | 4 | 6.5 ± 0.1 | 25.3 ± 1.2 | 22.7 ± 0.2 | 59.3 ± 2.9 |
| | −/− | 3h[e] | 3 | 7.2 ± 0.1* | 22.9 ± 1.0 | 24.1 ± 0.3* | 42.1 ± 2.0 |
| Liver | +/− | PBS[d] | 4 | ND | ND | ND | ND |
| | −/− | PBS[d] | 4 | ND | ND | ND | ND |
| | −/− | 3h[e] | 3 | ND | ND | ND | ND |

TABLE 3-continued

Effect of compound 3h on cerebrum, cerebellum, and liver ganglioside distribution in p-15 Sandhoff mouse.

| | Hex b Genotype | Treatment | n[c] | GT1b Percent | GT1b Concentration | GQ1b Percent | GQ1b Concentration |
|---|---|---|---|---|---|---|---|
| Cerebrum | +/− | PBS[d] | 4 | 27.0 ± 0.3 | 131.7 ± 4.3 | 6.9 ± 0.1 | 33.8 ± 0.9 |
| | −/− | PBS[d] | 4 | 26.2 ± 0.5 | 131.3 ± 3.2 | 6.5 ± 0.1 | 32.4 ± 0.5 |
| | −/− | 3h[e] | 3 | 27.8 ± 0.1* | 119.8 ± 3.3 | 7.7 ± 0.1** | 33.3 ± 0.7 |
| Cerebellum | +/− | PBS[d] | 4 | 30.8 ± 1.0 | 114.6 ± 3.5 | 12.0 ± 0.6 | 44.7 ± 2.1 |
| | −/− | PBS[d] | 4 | 29.1 ± 0.1 | 113.7 ± 5.3 | 10.6 ± 0.5 | 41.1 ± 1.1 |
| | −/− | 3h[e] | 3 | 29.7 ± 0.8 | 94.4 ± 3.9* | 12.9 ± 0.1 | 41.3 ± 3.8 |
| Liver | +/− | PBS[d] | 4 | ND | ND | ND | ND |
| | −/− | PBS[d] | 4 | ND | ND | ND | ND |
| | −/− | 3h[e] | 3 | ND | ND | ND | ND |

[a]Values are expressed as the mean ± standard error of the mean (SEM).
[b]Total sialic acid content was determined by the resorcinol assay. Percent distribution and concentrations of individual gangliosides were determined by densitometric scanning of HPTLC plates.
[c]n, the number of independent samples per group.
[d]Mice were injected daily from p-9 to p-15 with 1x Phosphate Buffer Saline.
[e]Mice were injected daily from p-9 to p-15 with 3h (EtDO-PIP2 oxalate) at 60 mg/kg/day.
*Significantly different from the PBS-treated −/− group at $P < 0.05$ using the student's t-test.
**Significantly different from the PBS-treated −/− group at $P < 0.01$ using the student's t-test.
ND, not detectable; 3h, ethylenedioxy-PIP2 oxalate The influence of compound 3h on the qualitative and quantitative distribution of brain gangliosides is shown in Table 3. Gangliosides that were undetectable or represented less than 1% of the total distribution (such as GD3 in cerebrum) were omitted from the analysis. Ganglioside GM2 comprised about 5% of ganglioside sialic acid content in p-15 Hexb −/− mouse cerebrum and cerebellum (Table 3). Compound 3h reduced GM2 content by 52% and 53%, respectively, in cerebrum and cerebellum of Hexb −/− mice. GM1, GD1a, GD1b, and GT1b content were also significantly reduced in cerebrum of Hexb −/− mice treated with 3h (Table 2). GD3, GD1b, and GT1b were significantly reduced in cerebellum of Hexb −/− mice treated with compound 3h (Table 3). In normal and Sandhoff mouse liver, GM2 containing N-glycolyl-neuraminic acid (NGNA) is the primary ganglioside. NGNA-GM2 content was significantly reduced by 45% in Hexb −/− mice treated with compound 3h compared to PBS-treated Hexb −/− controls (Table 2).

Compound 3h also influenced the storage of asialo GM2 (GA2). GA2 is undetectable in normal mouse brain and liver (Table 4). GA2 in liver resolved as a doublet, similar to NGNA-GM2. Compound 3h reduced GA2 in Hexb −/− liver, but this difference was not significant (p=0.06). There were no differences in neutral and acidic lipid content for Sandhoff mice treated with PBS or compound 3h (Table 4).

TABLE 4

Neutral and acidic lipid content in p-15 Sandhoff mice treated with compound 3 h

| | | Cerebrum | | |
|---|---|---|---|---|
| | | +/− | −/− | 3 h |
| Neutral Lipids[b] | | | | |
| | TG | ND | ND | ND |
| | Chol | 5.35 ± 0.09 | 5.22 ± 0.11 | 5.13 ± 0.11 |
| | Cer | 0.59 ± 0.01 | 0.56 ± 0.02 | 0.59 ± 0.05 |
| | CB | Trace | Trace | Trace |
| | PE | 9.95 ± 0.35 | 9.77 ± 0.65 | 9.11 ± 0.58 |
| | PC | 5.55 ± 0.33 | 5.91 ± 0.74 | 5.02 ± 0.91 |
| | SM | 0.94 ± 0.07 | 0.87 ± 0.07 | 0.83 ± 0.09 |
| | GA2 | ND | 0.70 ± 0.03 | 0.51 ± 0.01** |
| Acidic Lipids | | | | |
| | CL | 1.63 ± 0.03 | 1.70 ± 0.07 | 1.62 ± 0.11 |
| | Sulf | 0.50 ± 0.22 | 0.38 ± 0.02 | 0.44 ± 0.06 |
| | PS | 4.21 ± 0.22 | 4.38 ± 0.30 | 4.08 ± 0.14 |
| | Pl | 2.20 ± 0.06 | 2.22 ± 0.12 | 2.14 ± 0.12 |
| | | Cerebellum | | |
| | | +/− | −/− | 3 h |
| Neutral Lipids[b] | | | | |
| | TG | ND | ND | ND |
| | Chol | 4.00 ± 028 | 4.70 ± 0.55 | 3.55 ± 0.33 |
| | Cer | 2.23 ± 0.49 | 1.02 ± 0.17 | 1.54 ± 0.29 |
| | CB | 2.11 ± 0.08 | 1.81 ± 0.14 | 1.61 ± 0.04 |
| | PE | 3.34 ± 0.63 | 5.34 ± 1.31 | 3.12 ± 0.94 |
| | PC | 3.70 ± 0.30 | 4.93 ± 0.81 | 3.68 ± 0.34 |
| | SM | 0.34 ± 0.03 | 0.41 ± 0.05 | 0.43 ± 0.04 |
| | GA2 | ND | 0.71 ± 0.04 | 0.55 ± 0.01* |
| Acidic Lipids | | | | |
| | CL | 4.45 ± 0.15 | 3.63 ± 0.24 | 4.16 ± 0.09 |
| | Sulf | 2.33 ± 029 | 1.97 ± 0.19 | 1.81 ± 0.56 |
| | PS | 5.91 ± 0.16 | 5.69 ± 0.13 | 5.37 ± 0.35 |
| | Pl | 1.75 ± 0.04 | 1.82 ± 0.04 | 1.57 ± 0.11 |
| | | Liver | | |
| | | +/− | −/− | 3 h |
| Neutral Lipids[b] | | | | |
| | TG | 1.34 ± 0.28 | 0.06 ± 0.03 | 0.07 ± 0.07 |
| | Chol | 1.43 ± 0.02 | 1.37 ± 0.04 | 1.48 ± 0.07 |
| | Cer | 4.37 ± 0.29 | 4.49 ± 0.08 | 4.01 ± 0.18 |
| | CB | ND | ND | ND |
| | PE | 6.65 ± 0.18 | 5.22 ± 0.16 | 5.27 ± 0.94 |
| | PC | 3.75 ± 0.10 | 2.27 ± 0.09 | 2.73 ± 0.33 |
| | SM | 0.99 ± 0.07 | 1.20 ± 0.02 | 1.34 ± 0.04 |
| | GA2 | ND | 1.31 ± 0.07 | 1.10 ± 0.05 |

TABLE 4-continued

Neutral and acidic lipid content in p-15 Sandhoff mice treated with compound 3 h

| Acidic Lipids | | | |
|---|---|---|---|
| CL | 1.51 ± 0.22 | 2.02 ± 0.26 | 2.88 ± 0.35 |
| Sulf | ND | ND | ND |
| PS | 0.90 ± 0.05 | 1.03 ± 0.07 | 1.17 ± 0.06 |
| PI | 2.50 ± 0.14 | 2.46 ± 0.12 | 2.54 ± 0.10 |

[a]Values are expressed as mg/100 mg dry weight. N = 3-4 mice per group.
[b]Concentrations of individual lipids were determined by densitometric scanning of HPTLC plates.
*Significantly different from the PBS-treated −/− group at P < 0.05 using the student's t-test.
**Significantly different from the PBS-treated −/− group at P < 0.01 using the student's t-test.
ND, not detectable; 3 h, EtDO-PIP2.

The results summarized above show that a daily injection of compound 3h from postnatal day 9 to 15 significantly reduced the total content of brain and liver gangliosides in SD (Hexb −/−) mice. Compound 3h also significantly reduced the accumulation of GM2 and GA2 in cerebrum, cerebellum, and in liver indicating a systemic therapeutic response. In contrast to NB-DNJ (miglustat), which is known to reduce mouse body weight (22, 25), no adverse effects of compound 3h were detected on body weight over the treatment period. The reduction of total brain gangliosides, and of GM2 and GA2 content, in the Hexb −/− mice was obtained with a compound 3h dosage of 60 mg/kg/day. Although the reductions in mouse brain ganglioside content attributed to compound 3h were similar to those seen previously using the NB-DNJ or NB-DGJ imino sugars, the therapeutic dosages used in the studies with the imino sugars ranged from 400-1200 mg/kg body weight (23, 29, 32, 33).

As demonstrated above, various compounds of structural formula (I) are active in the brain. The novel GCS inhibitors are designed to lower or eliminate their recognition as substrates for the MDR1 transporter by comparison of selected physical properties to drugs known to cross the BBB. Several compounds retained nanomolar activity as GCS inhibitors in both broken cell enzyme and whole cell assays. Compound 3h is a particularly poor substrate for the MDR1 protein relative to the other analogs using two in vitro assays based on the stable expression of MDR1. Compound 3h also demonstrates significant in vivo activity in lowering brain GlcCer levels after 3 days of intraperitoneal administration. The decrease in brain GlcCer is in contrast to eliglustat tartrate, which had no discernable effect on brain GlcCer when administered in parallel. Compound 3h enters the brain and reduces GlcCer as illustrated in the following schema.

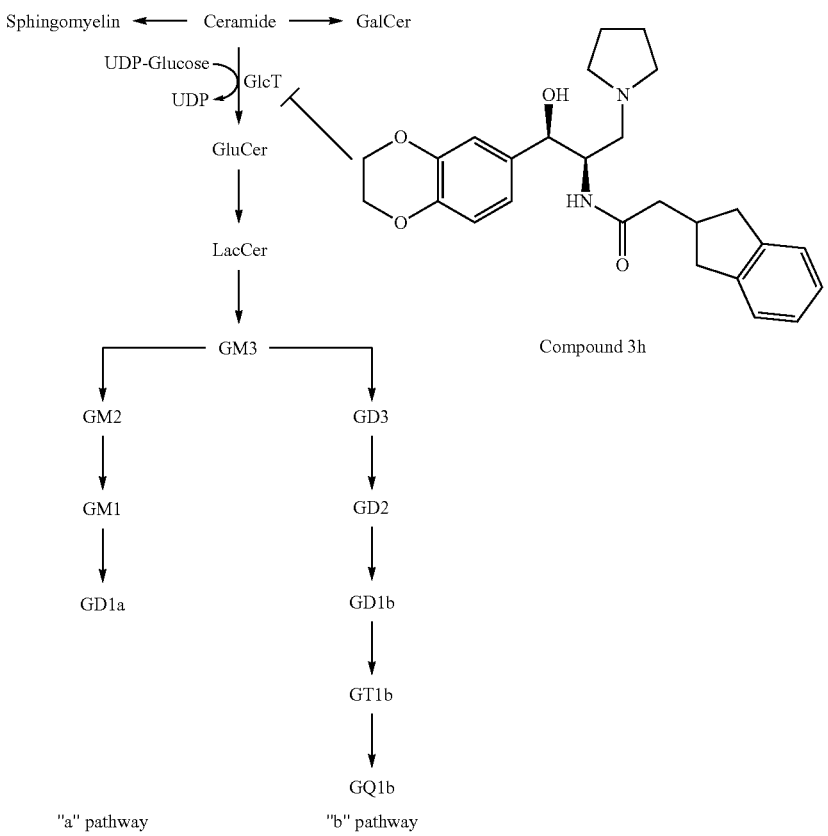

Compounds of structural formula (I), and particularly compound 3h, satisfy the properties of high inhibitory activity against GCS and limited MDR1 affinity. Because synthesis inhibition for the treatment of glycosphingolipidoses by GCS inhibitors is now well established on both experimental and clinical grounds, the identification of new compounds that are active within brain is an advance in the art.

METHODS AND COMPOSITIONS

The present invention provides GCS inhibitors, as exemplified by compounds of structural formula (I), for the treatment of a variety of diseases and conditions wherein inhibition of GCS has a beneficial effect. In one embodiment, the present invention relates to a method of treating an individual suffering from a disease or condition wherein inhibition of the GCS provides a benefit comprising administering a therapeutically effective amount of a compound of structural formula (I) to an individual in need thereof.

The compounds of structural formula (I) therefore can be used to treat a variety of diseases and conditions where inhibition of GCS provides a benefit. Examples of such diseases and condition include, but are not limited to, Tay-Sachs disease, type I, II, and III Gaucher disease, Sandhoff disease, and Fabry's disease; Parkinson's disease (J. R. Mazzulli et al., Cell 146:37-52, Jul. 8, 2011); type 2 diabetes; renal hypertrophy or hyperplasia associated with diabetic nephropathy; elevated plasma TNF-α; elevated blood glucose levels; elevated glycated hemoglobin levels; lupus; and a glomerular disease selected from the group consisting of mesangial proliferative glomerulonephritis, collapsing glomerulopathy, proliferative lupus nephritis, crescentic glomerulonephritis, and membranous nephropathy.

A compound of structural formula (I) also can be used to treat disorders involving cell growth and division, including cancer, collagen vascular diseases, atherosclerosis, and the renal hypertrophy of diabetic individuals (U.S. Pat. Nos. 6,916,802 and 5,849,326, each incorporated herein by reference); to inhibit the growth of arterial epithelial cells (U.S. Pat. Nos. 6,916,802 and 5,849,326, each incorporated herein by reference); to treat patients suffering from infections (M. Svensson et al., *Infect. And Immun.,* 62:4404-4410 (1994)); to prevent a host, i.e., patient, from generating antibodies against the tumor (J. Inokuchi et al., *Cancer Lett.,* 38:23-30 (1987); and to treat tumors (S. Hakomori *Cancer Cells* 3:461-470 (1991).); J. Inokuchi et al., *Cancer Res.,* 50L6731-6737 (1990).); and (M. Ziche et al., *Lab Invest.,* 67:711-715 (1992)). A compound of structural formula (I) further can be used to treat a polycystic kidney disease, including both autosomal dominant and recessive forms (T. A. Natoli et al., *Nat. Med.* 16:788-792 (2010)).

A method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of GCS provides a benefit, packaged separately or together, and an insert having instructions for using these active agents.

In many embodiments, a compound of structural formula (I) is administered in conjunction with a second therapeutic agent useful in the treatment of a disease or condition wherein inhibition of GCS provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, enzyme replacement therapy, gene therapy, and isofagomine.

In a method of treating type 2 diabetes, the second therapeutic agent can be one or more of insulin (e.g., NOVOLIN®, NOVOLOG®, VELOSULIN®); a sulfonylurea (e.g., DIABINESE®, GLUCOTROL®, GLUCOTROL XL®, DIABETA®, AMARYL®, ORINASE®, TOLINASE®, MICRONASE®, and GLYNASE®); metformin; an [alpha]-glucosidase inhibitor (e.g., GLYSET®); a thiazolidinedione (e.g., ACTOS® and AVANDIA®); nateglinide (STARLIX®); repaglinide (PRANDIN®), and combination drugs such as AVANDAMET® (AVANDIA® and metformin).

In a method of treating Parkinson's disease, the second therapeutic agent can be one or more of carbidopa/levodopa therapy; a dopamine agonist (apomorphine hydrochloride, bromocriptine, rotigotine, pramipexole, ropinirole, pergolide), an anticholinergic (benzotropine mesylate, trihexyphenidyl hydrochloride, procyclidine), an MAO-B inhibitor (selegiline, rasagiline), a COMT inhibitor (entacapone, tulcapone), and other medications including non-prescription, over-the-counter therapeutics (amantadine, rivastigmine tartrate, creatine, coenzyme Q10).

The diseases and conditions that can be treated in accordance to the invention include, for example, Gaucher disease, Fabry disease, Tay-Sachs disease, and diabetes. In particular, type II and type III Gaucher disease can be treated because various compounds of structural formula (I) are capable of crossing the BBB. Prior GCS inhibitors either were incapable of crossing the BBB or had low potency and selectivity, and accordingly various diseases associated with glycolipid accumulation could not be treated.

In the present method, a therapeutically effective amount of one or more compound of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the GCS inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present GCS inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a GCS inhibitor of structural formula (I), or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the GCS inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior GCS inhibitors possessed properties that hindered their development as therapeutic agents. In accordance with an important feature of the present invention, compounds of structural formula (I) were synthesized and evaluated as inhibitors for GCS, and, in particular, for having an ability to cross the BBB. The present GCS inhibitors are characterized by inhibition of GCS at low nanomolar concentrations, high specificity, and the absence of β-glucocerebrosidase binding.

REFERENCES

1. N. W. Barton et al., *N Engl J Med* 324, 1464-1470, (1991).
2. N. S. Radin, *Glycoconj J* 13, 153-157, (1996).
3. J. A. Shayman et al., *Methods Enzymol* 311, 373-387, (2000).
4. N. J. Weinreb et al., *Am J Hematol* 80, 223-229, (2005).
5. J. A. Shayman, *Drugs of the Future* 35, 613-621, (2010).
6. E. Lukina et al., *Blood* 116(20):4095-8, (2010).
7. A. Abe et al., *J Clin Invest* 105, 1563-1571, (2000).
8. Y. Liu et al., *The Journal of clinical investigation* 103, 497-505, (1999).
9. J. A. Shayman et al., *Methods Enzymol* 311, 42-49, (2000).
10. L. Shu et al., *J Biol Chem* 278, 31419-31425, (2003).
11. C. Shu et al., *The Journal of pharmacology and experimental therapeutics* 301, 820-829, (2002).
12. D. S. Wishart et al., *Nucleic Acids Res* 36, D901-906, (2008).
13. M. Jimbo et al., *J Biochem-Tokyo* 127, 485-491, (2000).
14. C. A. Lipinski et al., *Advanced Drug Delivery Reviews* 23, 3-25, (1997).
15. P. Garberg et al., *Toxicol In Vitro* 19, 299-334, (2005).
16. Q. Wang et al., *Int J Pharm* 288, 349-359, (2005).
17. K. M. Mahar Doan et al., *The Journal of pharmacology and experimental therapeutics* 303, 1029-1037, (2002).
18. P. D. Leeson et al., *J Med Chem* 47, 6338-6348 (2004).
19. H. Pajouhesh et al., *NeuroRx* 2, 541-553, (2005).
20. R. Cecchelli et al., *Nat Rev Drug Discov* 6, 650-661 (2007).
21. S. Lundquist et al., *Pharm Res* 19, 976-981 (2002).
22. U. Andersson et al., *Biochemical pharmacology* vol. 59, no. 7, pp. 821-829 (2000).
23. R. C. Baek et al., *Neurochemistry international*, vol. 52, no. 6, pp. 1125-1133 (2008).
24. R. C. Baek et al., *Lipids*, vol. 44, no. 3, pp. 197-205 (2009).
25. C. A. Denny et al., *Journal of neuroscience research*, vol. 83, no. 6, pp. 1028-1038 (2006).
26. C. A. Denny et al., *Journal of neurochemistry*, vol. 113, no. 6, pp. 1525-1535 (2010).
27. H. Galjaard, *Annals of Clinical Biochemistry*, vol. 16, no. 6, pp. 343-353 (1979).
28. E. C. Hauser et al., *Biochemical genetics*, vol. 42, no. 7-8, pp. 241-257 (2004).
29. M. Jeyakumar et al., *Blood*, vol. 97, no. 1, pp. 327-329 (2001).
30. M. Jeyakumar et al., *Neuropathology and applied neurobiology*, vol. 28, no. 5, pp. 343-357 (2002).
31. M. Jeyakumar et al., *Brain: a journal of neurology*, vol. 126, no. Pt 4, pp. 974-987 (2003).
32. J. L. Kasperzyk et al., *Journal of neurochemistry*, vol. 89, no. 3, pp. 645-653 (2004).
33. J. L. Kasperzyk et al., *Journal of lipid research*, vol. 46, no. 4, pp. 744-751 (2005).
34. T. Kolter et al., *Biochimica et Biophysica Acta*, vol. 1758, no. 12, pp. 2057-2079 (2006).
35. S. Kyrkanides et al., *Journal of neuroimmunology*, vol. 203, no. 1, pp. 50-57 (2008).
36. L. J. Macala et al., *Journal of lipid research*, vol. 24, no. 9, pp. 1243-1250 (1983).
37. D. Phaneuf et al., *Human molecular genetics*, vol. 5, no. 1, pp. 1-14 (1996).
38. K. Sango et al., *Nature genetics*, vol. 11, no. 2, pp. 170-176 (1995).
39. T. N. Seyfried et al., *Biochemical genetics*, vol. 17, no. 1-2, pp. 43-55 (1979).
40. T. N. Seyfried et al., *Biochemical genetics*, vol. 18, no. 11-12, pp. 1229-1237 (1980).

What is claimed:
1. A compound having a structure

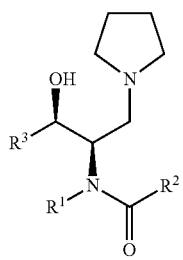

wherein $R^1$ is H or $C_{1-3}$alkyl;
$R^2$ is

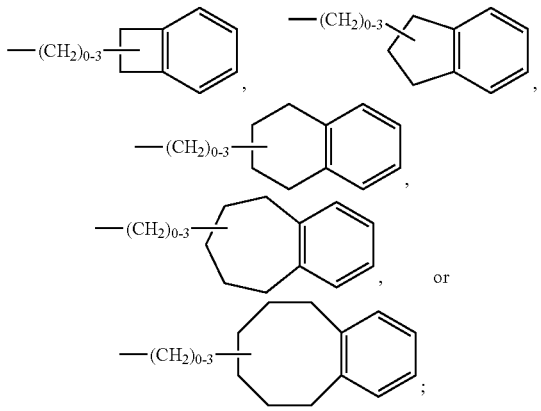

and

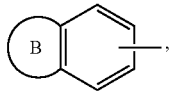

$R^3$ is
wherein the fused ring B is a five- or six-membered ring, saturated or partially or fully unsaturated, comprising carbon atoms and one or two heteroatoms selected from O, S, and $NR^a$, and wherein the phenyl ring is optionally substituted with one or two substituents selected from the group consisting of halo, $C_{1-3}$alkyl, $OR^a$, $CO_2R^a$, halomethyl, halomethoxy, cyano, nitro, and $N(R^a)_2$;
or a pharmaceutically acceptable salt, solvate, hydrate, or prodrug thereof, and $R^a$ independently is H or $C_{1-3}$alkyl.

2. The compound of claim 1 wherein $R^1$ is H, —$CH_3$, —$CH_2CH_3$, —$CH_2CH_2CH_3$, or

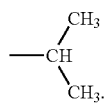

3. The compound of claim 1 wherein a fused B ring of $R^3$ is selected from the group consisting of cyclopentyl, cyclohexyl, cyclopentenyl, cyclohexenyl, phenyl, furanyl, thienyl, 2H-pyrrolyl, pyrrolyl, 2-pyrrolinyl, 3-pyrrolinyl, pyrrolidinyl, 1,3-dioxolanyl, oxazolyl, thiazolyl, imidazolyl, 2-imidazolinyl, imidazolidinyl, pyrazolyl, 2-pyrazolinyl, pyrazolidinyl, isoxazolyl, isothiazolyl, 3H-pyrrolyl, 1,2-dithiolyl, 1,3-dithiolyl, 3H-1,2-oxathiolyl, 5H-1,2,5-oxathiazolyl, 1,3-oxathiolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, piperazinyl, 1,3,5-triazinyl, 1,3,5-trithianyl, 2-pyronyl, 4-pyronyl, 1,2-dioxinyl, 1,3-dioxinyl, 1,2-dioxinyl, 1,3-dioxinyl, 4H-1,3-oxazinyl, 2H-1,3-oxazinyl, 6H-1,2-oxazinyl, 4H-1,4-oxazinyl, 2H-1,2-oxazinyl, 1,4-oxazinyl, p-isoxazinyl, and o-isoxazinyl.

4. The compound of claim 1 wherein $R^3$ is

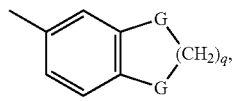

q is an integer 1 or 2, and G, independently, is O, S, or $NR^a$.

5. The compound of claim 4 wherein $R^3$ is

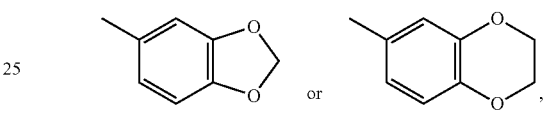

optionally substituted with halo, $C_{1-3}$alkyl, $OR^a$, $CO_2R^a$, halomethyl, halomethoxy, cyano, nitro, or $N(R^a)_2$.

6. A compound selected from the group consisting of N-((1R,2R)-1-(2,3-dihydrobenzo[b][1,4]dioxin-6-yl)-1-hydroxy-3-(pyrrolidin-1-yl)propan-2-yl)cinnamamide, N-((1R,2R)-1-(2,3-dihydrobenzo[b][1,4]dioxin-6-yl)-1-hydroxy-3-(pyrrolidin-1-yl)propan-2-yl)-2-phenylcyclopropanecarboxamide, 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide, N-((1R,2R)-1-(2,3-dihydrobenzo[b][1,4]dioxin-6-yl)-1-hydroxy-3-(pyrrolidin-1-yl)propan-2-yl)-2,3-dihydro-1H-indene-2-carboxamide, N-((1R,2R)-1-(2,3-dihydrobenzo[b][1,4]dioxin-6-yl)-1-hydroxy-3-(pyrrolidin-1-yl)propan-2-yl)-N-methyl-3-phenylpropanamide, N-((1R,2R)-1-hydroxy-1-(2-methoxyphenyl)-3-(pyrrolidin-1-yl)propan-2-yl)octanamide, N-((1R,2R)-1-(3-(dimethylamino)phenyl)-1-hydroxy-3-(pyrrolidin-1-yl)propan-2-yl)octanamide, N-((1R,2R)-1-(2,3-dihydrobenzo[b][1,4]dioxin-6-yl)-1-hydroxy-3-(pyrrolidin-1-yl)propan-2-yl)-3-(3-fluorophenyl)propanamide, N-((1R,2R)-1-(2,3-dihydrobenzo[b][1,4]dioxin-6-yl)-1-hydroxy-3-(pyrrolidin-1-yl)propan-2-yl)-3-(4-fluorophenyl)propanamide, N-((1R,2R)-1-(2,3-dihydrobenzo[b][1,4]dioxin-6-yl)-1-hydroxy-3-(pyrrolidin-1-yl)propan-2-yl)-3-phenylbutanamide (mixture of diastereomers), N-((1R,2R)-1-(2,3-dihydrobenzo[b][1,4]dioxin-6-yl)-1-hydroxy-3-(pyrrolidin-1-yl)propan-2-yl)-3-(2-methoxyphenyl)propanamide, N-((1R,2R)-1-(2,3-dihydrobenzo[b][1,4]dioxin-6-yl)-1-hydroxy-3-(pyrrolidin-1-yl)propan-2-yl)-2-(phenylamino)acetamide, 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide oxylate monohydrate, and N-((1R,2R)-1-(2,3-dihydrobenzo[b][1,4]dioxin-6-yl)-1-hydroxy-3-(pyrrolidin-1-yl)propan-2-yl)-2-phenylacetamido,
or a pharmaceutically acceptable salt thereof.

7. A pharmaceutical composition comprising a compound of claim 1 and a pharmaceutically acceptable carrier or vehicle.

* * * * *